US010271424B2

(12) United States Patent
Dragone et al.

(10) Patent No.: US 10,271,424 B2
(45) Date of Patent: *Apr. 23, 2019

(54) TAMPER-RESPONDENT ASSEMBLIES WITH IN SITU VENT STRUCTURE(S)

(71) Applicant: INTERNATIONAL BUSINESS MACHINES CORPORATION, Armonk, NY (US)

(72) Inventors: Silvio Dragone, Rueschlikon (CH); Stefano S. Oggioni, Segrate (IT); William Santiago-Fernandez, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 250 days.

This patent is subject to a terminal disclaimer.

(21) Appl. No.: 15/275,762

(22) Filed: Sep. 26, 2016

(65) Prior Publication Data

US 2018/0092204 A1    Mar. 29, 2018

(51) Int. Cl.
*H05K 1/00* (2006.01)
*H05K 1/02* (2006.01)
(Continued)

(52) U.S. Cl.
CPC ........... *H05K 1/0275* (2013.01); *G01N 27/20* (2013.01); *G06F 21/87* (2013.01); *H05K 1/0272* (2013.01);
(Continued)

(58) Field of Classification Search
CPC .................................................. H05K 1/0275
See application file for complete search history.

(56) References Cited

U.S. PATENT DOCUMENTS 3,165,569 A   1/1965  Bright et al.
4,160,503 A   7/1979  Ohlbach
(Continued)

FOREIGN PATENT DOCUMENTS

CN   2014-30639 Y    3/2010
CN   10-4346587 A    2/2015
(Continued)

OTHER PUBLICATIONS

Holm, Ragnar, "Electric Contacts: Theory and Application", Spinger-Verlag, New York, 4th Edition, 1981 (pp. 10-19).
(Continued)

*Primary Examiner* — Stephen W Jackson
(74) *Attorney, Agent, or Firm* — Margaret A. McNamara, Esq.; Kevin P. Radigan, Esq.; Heslin Rothenberg Farley & Mesiti P.C.

(57) ABSTRACT

Vented tamper-respondent assemblies and methods of fabrication are provided which include a multilayer circuit board, a tamper-detection sensor, and an in situ vent structure. The tamper-detection sensor is embedded within the multilayer circuit board, and defines, at least in part, a secure volume associated with the multilayer circuit board. The in situ vent structure is formed within the multilayer circuit board, and includes at least one vent channel. The vent channel(s) is in fluid communication with a space within the secure volume to facilitate venting the space of the secure volume. The space within the secure volume may accommodate, for instance, one or more electronic components to be protected, and the at least one vent channel may, for instance, allow air pressure within the space of the secure volume to equalize with air pressure external to the tamper-respondent assembly.

20 Claims, 24 Drawing Sheets

(51) Int. Cl.
- *H05K 1/18* (2006.01)
- *G01N 27/20* (2006.01)
- *G06F 21/87* (2013.01)
- *H05K 3/46* (2006.01)

(52) U.S. Cl.
CPC ........... *H05K 1/185* (2013.01); *H05K 3/4697* (2013.01); *H05K 2201/10151* (2013.01)

(56) References Cited

U.S. PATENT DOCUMENTS

| | | |
|---|---|---|
| 4,211,324 A | 7/1980 | Ohlbach |
| 4,324,823 A | 4/1982 | Ray, III |
| 4,496,900 A | 1/1985 | Di Stefano et al. |
| 4,516,679 A | 5/1985 | Simpson |
| 4,593,384 A | 6/1986 | Kleijne |
| 4,609,104 A | 9/1986 | Kasper et al. |
| 4,653,252 A | 3/1987 | Van de Haar et al. |
| 4,677,809 A | 7/1987 | Long et al. |
| 4,691,350 A | 9/1987 | Kleijne et al. |
| 4,807,284 A | 2/1989 | Kleijne |
| 4,811,288 A | 3/1989 | Kleijne et al. |
| 4,860,351 A | 8/1989 | Weingart |
| 4,865,197 A | 9/1989 | Craig |
| 5,009,311 A | 4/1991 | Schenk |
| 5,027,397 A | 6/1991 | Double et al. |
| 5,060,114 A | 10/1991 | Feinberg et al. |
| 5,075,822 A | 12/1991 | Baumler et al. |
| 5,117,457 A | 5/1992 | Comerford et al. |
| 5,159,629 A | 10/1992 | Double et al. |
| 5,185,717 A | 2/1993 | Mori |
| 5,201,868 A | 4/1993 | Johnson |
| 5,201,879 A | 4/1993 | Steele et al. |
| 5,211,618 A | 5/1993 | Stoltz |
| 5,239,664 A | 8/1993 | Verrier et al. |
| 5,389,738 A | 2/1995 | Piosenka et al. |
| 5,406,630 A | 4/1995 | Piosenka et al. |
| 5,506,566 A | 4/1996 | Oldfield et al. |
| 5,568,124 A | 10/1996 | Joyce et al. |
| 5,594,439 A | 1/1997 | Swanson |
| 5,675,319 A | 10/1997 | Rivenberg et al. |
| 5,715,652 A | 2/1998 | Stahlecker |
| 5,761,054 A | 6/1998 | Kuhn |
| 5,813,113 A | 9/1998 | Stewart et al. |
| 5,858,500 A | 1/1999 | MacPherson |
| 5,880,523 A | 3/1999 | Cadelore |
| 5,988,510 A | 11/1999 | Tuttle et al. |
| 6,121,544 A | 9/2000 | Petsinger |
| 6,195,267 B1 | 2/2001 | MacDonald, Jr. et al. |
| 6,201,296 B1 | 3/2001 | Fries et al. |
| 6,261,215 B1 | 7/2001 | Imer |
| 6,301,096 B1 | 10/2001 | Wozniczka |
| 6,384,397 B1 | 5/2002 | Takiar et al. |
| 6,396,400 B1 | 5/2002 | Epstein, III et al. |
| 6,424,954 B1 | 7/2002 | Leon |
| 6,438,825 B1 | 8/2002 | Kuhm |
| 6,469,625 B1 | 10/2002 | Tomooka |
| 6,473,995 B2 | 11/2002 | Miyakawa et al. |
| 6,512,454 B2 | 1/2003 | Miglioli et al. |
| 6,686,539 B2 | 2/2004 | Farquhar et al. |
| 6,746,960 B2 | 6/2004 | Goodman et al. |
| 6,798,660 B2 | 9/2004 | Moss et al. |
| 6,853,093 B2 | 2/2005 | Cohen et al. |
| 6,879,032 B2 | 4/2005 | Rosenau et al. |
| 6,929,900 B2 | 8/2005 | Farquhar et al. |
| 6,946,960 B2 | 9/2005 | Sisson et al. |
| 6,957,345 B2 | 10/2005 | Cesana et al. |
| 6,970,360 B2 | 11/2005 | Sinha |
| 6,985,362 B2 | 1/2006 | Mori et al. |
| 6,991,961 B2 | 1/2006 | Hubbard et al. |
| 6,996,953 B2 | 2/2006 | Perreault et al. |
| 7,005,733 B2 | 2/2006 | Kommerling et al. |
| 7,015,823 B1 | 3/2006 | Gillen et al. |
| 7,054,162 B2 | 5/2006 | Benson et al. |
| 7,057,896 B2 | 6/2006 | Matsuo et al. |
| 7,094,143 B2 | 8/2006 | Wolm et al. |
| 7,094,459 B2 | 8/2006 | Takahashi |
| 7,095,615 B2 | 8/2006 | Nichols |
| 7,156,233 B2 | 1/2007 | Clark et al. |
| 7,180,008 B2 | 2/2007 | Heitmann et al. |
| 7,189,360 B1 | 3/2007 | Ho et al. |
| 7,214,874 B2 | 5/2007 | Dangler et al. |
| 7,247,791 B2 | 7/2007 | Kulpa |
| 7,304,373 B2 | 12/2007 | Taggart et al. |
| 7,310,737 B2 | 12/2007 | Patel et al. |
| 7,465,887 B2 | 12/2008 | Suzuki et al. |
| 7,475,474 B2 | 1/2009 | Heitmann et al. |
| 7,515,418 B2 | 4/2009 | Straznicky et al. |
| 7,549,064 B2 | 6/2009 | Elbert et al. |
| 7,640,658 B1 | 1/2010 | Pham et al. |
| 7,643,290 B1 | 1/2010 | Narasimhan et al. |
| 7,663,883 B2 | 2/2010 | Shirakami et al. |
| 7,672,129 B1 | 3/2010 | Ouyang et al. |
| 7,731,517 B2 | 6/2010 | Lee et al. |
| 7,746,657 B2 | 6/2010 | Oprea et al. |
| 7,760,086 B2 | 7/2010 | Hunter et al. |
| 7,768,005 B2 | 8/2010 | Condorelli et al. |
| 7,783,994 B2 | 8/2010 | Ball et al. |
| 7,787,256 B2 | 8/2010 | Chan et al. |
| 7,868,411 B2 | 1/2011 | Kim et al. |
| 7,898,413 B2 | 3/2011 | Hsu et al. |
| 7,901,977 B1 | 3/2011 | Angelopoulos et al. |
| 7,947,911 B1 | 5/2011 | Pham et al. |
| 7,978,070 B2 | 7/2011 | Hunter |
| 8,006,101 B2 | 8/2011 | Crawford |
| 8,084,855 B2 | 12/2011 | Lower et al. |
| 8,094,450 B2 | 1/2012 | Cole |
| 8,101,267 B2 | 1/2012 | Samuels et al. |
| 8,133,621 B2 | 3/2012 | Wormald et al. |
| 8,199,506 B2 | 6/2012 | Janik et al. |
| 8,287,336 B2 | 10/2012 | Dangler et al. |
| 8,325,486 B2 | 12/2012 | Arshad et al. |
| 8,516,269 B1 | 8/2013 | Hamlet et al. |
| 8,589,703 B2 | 11/2013 | Lee et al. |
| 8,646,108 B2 | 2/2014 | Shiakallis et al. |
| 8,659,506 B2 | 2/2014 | Nomizo |
| 8,659,908 B2 | 2/2014 | Adams et al. |
| 8,664,047 B2 | 3/2014 | Lower et al. |
| 8,716,606 B2 | 5/2014 | Kelley et al. |
| 8,797,059 B2 | 8/2014 | Boday et al. |
| 8,836,509 B2 | 9/2014 | Lowy |
| 8,853,839 B2 | 10/2014 | Gao et al. |
| 8,879,266 B2 | 11/2014 | Jarvis et al. |
| 8,890,298 B2 | 11/2014 | Buer et al. |
| 8,947,889 B2 | 2/2015 | Kelley et al. |
| 8,961,280 B2 | 2/2015 | Dangler et al. |
| 9,003,199 B2 | 4/2015 | Dellmo et al. |
| 9,011,762 B2 | 4/2015 | Seppa et al. |
| 9,052,070 B2 | 6/2015 | Davis et al. |
| 9,166,586 B2 | 10/2015 | Carapelli et al. |
| 9,298,956 B2 | 3/2016 | Wade et al. |
| 9,578,735 B2 * | 2/2017 | Fisher .................. H05K 1/0275 |
| 9,930,768 B2 * | 3/2018 | Fisher .................. H05K 1/0275 |
| 9,949,357 B2 * | 4/2018 | Fisher .................. H05K 1/0275 |
| 2001/0050425 A1 | 12/2001 | Beroz et al. |
| 2001/0056542 A1 | 12/2001 | Cesana et al. |
| 2002/0002683 A1 | 1/2002 | Benson |
| 2002/0068384 A1 | 6/2002 | Beroz et al. |
| 2002/0084090 A1 | 7/2002 | Farquhar |
| 2003/0009684 A1 | 1/2003 | Schwenck et al. |
| 2005/0068735 A1 | 3/2005 | Fissore et al. |
| 2005/0111194 A1 | 5/2005 | Sohn et al. |
| 2005/0180104 A1 | 8/2005 | Olesen et al. |
| 2006/0034731 A1 | 2/2006 | Lewis et al. |
| 2006/0049941 A1 | 3/2006 | Hunter et al. |
| 2006/0072288 A1 | 4/2006 | Stewart et al. |
| 2006/0196945 A1 | 9/2006 | Mendels |
| 2006/0218779 A1 | 10/2006 | Ooba et al. |
| 2007/0064396 A1 | 3/2007 | Oman et al. |
| 2007/0064399 A1 | 3/2007 | Mandel et al. |
| 2007/0108619 A1 | 5/2007 | Hsu |
| 2007/0211436 A1 | 9/2007 | Robinson et al. |
| 2007/0230127 A1 | 10/2007 | Peugh et al. |
| 2007/0268671 A1 | 11/2007 | Brandenburg et al. |

(56) References Cited

U.S. PATENT DOCUMENTS

| | | |
|---|---|---|
| 2008/0050512 A1 | 2/2008 | Lower et al. |
| 2008/0144290 A1 | 6/2008 | Brandt et al. |
| 2008/0159539 A1 | 7/2008 | Huang et al. |
| 2008/0160274 A1 | 7/2008 | Dang et al. |
| 2008/0191174 A1 | 8/2008 | Ehrensvard et al. |
| 2008/0251906 A1 | 10/2008 | Eaton et al. |
| 2009/0073659 A1 | 3/2009 | Peng et al. |
| 2009/0166065 A1 | 7/2009 | Clayton et al. |
| 2010/0088528 A1 | 4/2010 | Sion |
| 2010/0110647 A1 | 5/2010 | Hiew et al. |
| 2010/0177487 A1 | 7/2010 | Arshad et al. |
| 2010/0319986 A1 | 12/2010 | Bleau et al. |
| 2011/0001237 A1 | 1/2011 | Brun et al. |
| 2011/0038123 A1 | 2/2011 | Janik et al. |
| 2011/0103027 A1 | 5/2011 | Aoki et al. |
| 2011/0241446 A1 | 10/2011 | Tucholski |
| 2011/0299244 A1 | 12/2011 | Dede et al. |
| 2012/0050998 A1 | 3/2012 | Klum et al. |
| 2012/0117666 A1 | 5/2012 | Oggioni et al. |
| 2012/0140421 A1 | 6/2012 | Kirstine et al. |
| 2012/0319986 A1 | 6/2012 | Toh et al. |
| 2012/0170217 A1 | 7/2012 | Nishikimi et al. |
| 2012/0185636 A1 | 7/2012 | Leon et al. |
| 2012/0244742 A1 | 9/2012 | Wertz et al. |
| 2012/0256305 A1 | 10/2012 | Kaufmann et al. |
| 2012/0320529 A1 | 12/2012 | Loong et al. |
| 2013/0033818 A1 | 2/2013 | Hosoda et al. |
| 2013/0058052 A1 | 3/2013 | Arshad et al. |
| 2013/0104252 A1 | 4/2013 | Yanamadala et al. |
| 2013/0141137 A1 | 6/2013 | Krutzik et al. |
| 2013/0158936 A1 | 6/2013 | Rich et al. |
| 2013/0170217 A1 | 7/2013 | Lee |
| 2013/0208422 A1 | 8/2013 | Hughes et al. |
| 2013/0235527 A1 | 9/2013 | Wagner et al. |
| 2013/0283386 A1 | 10/2013 | Lee |
| 2014/0022733 A1 | 1/2014 | Lim et al. |
| 2014/0160679 A1 | 6/2014 | Kelty et al. |
| 2014/0184263 A1 | 7/2014 | Ehrenpfordt et al. |
| 2014/0204533 A1 | 7/2014 | Abeyasekera et al. |
| 2014/0321064 A1 | 10/2014 | Bose et al. |
| 2014/0325688 A1 | 10/2014 | Cashin et al. |
| 2015/0007427 A1 | 1/2015 | Dangler et al. |
| 2015/0163933 A1 | 6/2015 | Steiner |
| 2015/0235053 A1 | 8/2015 | Lee et al. |
| 2016/0005262 A1 | 1/2016 | Hirato et al. |
| 2016/0137548 A1 | 5/2016 | Cabral, Jr. et al. |
| 2016/0262253 A1 | 9/2016 | Isaacs et al. |
| 2016/0262270 A1 | 9/2016 | Isaacs et al. |
| 2017/0019987 A1 | 1/2017 | Dragone et al. |

FOREIGN PATENT DOCUMENTS

| | | |
|---|---|---|
| DE | 19816571 A1 | 10/1999 |
| DE | 19816572 A1 | 10/1999 |
| DE | 10-2012-203955 A1 | 9/2013 |
| EP | 0 056 360 A1 | 10/1993 |
| EP | 0 629 497 A2 | 12/1994 |
| EP | 1 184 773 A1 | 3/2002 |
| EP | 1 207 444 A2 | 5/2002 |
| EP | 1 734 578 A1 | 12/2006 |
| EP | 1 968 362 A2 | 9/2008 |
| EP | 2 104 407 A1 | 9/2009 |
| EP | 1 672 464 B1 | 4/2012 |
| EP | 2 560 467 A1 | 2/2013 |
| JP | 61-297035 A | 12/1986 |
| JP | 2000-238141 A | 9/2000 |
| JP | 2013-125807 A | 6/2013 |
| JP | 2013-140112 A | 7/2013 |
| WO | WO 1999/003675 A1 | 1/1999 |
| WO | WO 1999/021142 A1 | 4/1999 |
| WO | WO 2001/063994 A2 | 8/2001 |
| WO | WO 2003/012606 A2 | 2/2003 |
| WO | WO 2003/025080 A1 | 3/2003 |
| WO | WO 2004/040505 A1 | 5/2004 |
| WO | WO 2009/042335 A1 | 4/2009 |
| WO | WO 2009/092472 A1 | 7/2009 |
| WO | WO 2010/128939 A1 | 11/2010 |
| WO | WO 2013/004292 A1 | 1/2013 |
| WO | WO 2013/189483 A1 | 12/2013 |
| WO | WO 2014/086987 A2 | 6/2014 |
| WO | WO 2014/158159 A1 | 10/2014 |

OTHER PUBLICATIONS

Clark, Andrew J., "Physical Protection of Cryptographic Devices", Advanced in Cyprtology, Eurocrypt '87, Springer, Berlin Heidelberg (1987) (11 pages).

Halperin et al., "Latent Open Testing of Electronic Packaging", MCMC-194, IEEE (1994) (pp. 83-33).

Simek, Bob, "Tamper Restrictive Thermal Ventilation System for Enclosures Requiring Ventilation and Physical Security", IBM Publication No. IPCOM000008607D, Mar. 1, 1998 (2 pages).

Pamula et al., "Cooling of Integrated Circuits Using Droplet-Based Microfluidics", Association for Computing Machinery (ACM), GLSVLSI'03, Apr. 28-29, 2003 (pp. 84-87).

Saran et al., "Fabrication and Characterization of Thin Films of Single-Walled Carbon Nanotube Bundles on Flexible Plastic Substrates", Journal of the American Chemical Society, vol. 126, No. 14 (Mar. 23, 2004) (pp. 4462-4463).

Khanna P.K. et al., "Studies on Three-Dimensional Moulding, Bonding and Assembling of Low-Temperature-Cofired Ceramics MEMS and MST Applications." Materials Chemistry and Physics, vol. 89, No. 1 (2005) (pp. 72-79).

Drimer et al., "Thinking Inside the Box: System-Level Failures of Tamper Proofing", 2008 IEEE Symposium on Security and Privacy, (Feb. 2008) (pp. 281-295).

Loher et al., "Highly Integrated Flexible Electronic Circuits and Modules", 3rd International IEEE on Microsystems, Packaging, Assembly & Circuits Technology Conference (Oct. 22-24, 2008) (Abstract Only) (1 page).

Sample et al., "Design of an RFID-Based Battery-Free Programmable Sensing Platform", IEEE Transactions on Instrumentation and Measurement, vol. 57, No. 11, Nov. 2008 (pp. 2608-2615).

Jhang et al., "Nonlinear Ultrasonic Techniques for Non-Destructive Assessment of Micro Damage in Material: A Review", International Journal of Prec. Eng. & Manuf., vol. 10, No. 1, Jan. 2009 (pp. 123-135).

Anonymous, "Consolidated Non-Volatile Memory in a Chip Stack", IBM Technical Disclosure: IP.com No. IPCOM000185250, Jul. 16, 2009 (6 pages).

Isaacs et al., "Tamper Proof, Tamper Evident Encryption Technology", Pan Pacific Symposium SMTA Proceedings (2013) (9 pages).

Anonymous, "Selective Memory Encryption", IBM Technical Disclosure: IP.com IPCOM000244183, Nov. 20, 2015 (6 page).

Zhou et al., "Nonlinear Analysis for Hardware Trojan Detection", ICSPCC2015, IEEE (2015) (4 pages).

Harting Mitronics, "Saftey Caps for Payment Terminals", http://harting-mitronics.ch/fileadmin/hartingmitronics/case_studies/Saftey_caps_for_payment_terminals.pdf, downloaded Aug. 2016 (2 pages).

Dangler et al., "Tamper-Respondent Sensors with Formed Flexible Layer(s)", U.S. Appl. No. 14/865,551, filed Sep. 25, 2015 (113 pages).

Brodsky et al., "Overlapping, Discrete Tamper-Respondent Sensors", U.S. Appl. No. 14/865,572, filed Sep. 25, 2015 (114 pages).

Dangler et al., "Tamper-Respondent Assemblies with Region(s) of Increased Susceptibility to Damage", U.S. Appl. No. 14/865,591, filed Sep. 25, 2015 (114 pages).

Brodsky et al., "Circuit Boards and Electronic Packages with Embedded Tamper-Respondent Sensor", U.S. Appl. No. 14/865,610, filed Sep. 25, 2015 (43 pages).

Brodsky et al, "Tamper-Respondent Assemblies", U.S. Appl. No. 14/865,632, filed Sep. 25, 2015 (115 pages).

Brodksky et al., "Enclosure with Inner Tamper-Respondent Sensor(s)", U.S. Appl. No. 14/865,651, filed Sep. 25, 2015 (115 pages).

Fisher et al., "Enclosure with Inner Tamper-Respondent Sensor(s) and Physical Security Element(s)", U.S. Appl. No. 14/865,686, filed Sep. 25, 2015 (114 pages).

(56) References Cited

OTHER PUBLICATIONS

Brodsky et al., "Tamper-Respondent Assemblies with Bond Protection", U.S. Appl. No. 14/865,708, filed Sep. 25, 2015 (113 pages).
Brodsky et al., "Circuit Layouts of Tamper-Respondent Sensors", U.S. Appl. No. 14/886,179, filed Oct. 19, 2015 (113 pages).
Isaacs, Phillip Duane, "Tamper-Respondent Assembly with Protective Wrap(s) Over Tamper-Respondent Sensor(s)", U.S. Appl. No. 14/918,691, filed Oct. 21, 2015 (40 pages).
Brodsky et al., "Tamper-Respondent Assemblies with Bond Protection", U.S. Appl. No. 14/941,860, filed Nov. 16, 2015 (108 pages).
Fisher et al., "Enclosure with Inner Tamper-Respondent Sensor(s) and Physical Security Element(s)", U.S. Appl. No. 14/941,872, filed Nov. 16, 2015 (109 pages).
Brodsky et al, "Tamper-Respondent Assemblies", U.S. Appl. No. 14/941,887, filed Nov. 16, 2015 (109 pages).
Brodsky et al., "Circuit Boards and Electronic Packages with Embedded Tamper-Respondent Sensors", U.S. Appl. No. 14/941,908, filed Nov. 16, 2015 (41 pages).
Fisher et al., "Tamper-Respondent Assembly with Vent Structure", U.S. Appl. No. 14/955,283, filed Dec. 1, 2015 (61 pages).
Fisher et al., "Applying Pressure to Adhesive Using CTE Mismatch Between Components", U.S. Appl. No. 14/963,681, filed Dec. 9, 2015 (68 pages).
Brodsky et al., "Tamper-Respondent Assemblies with Enclosure-to-Board Protection", U.S. Appl. No. 14/974,036, filed Dec. 18, 2015 (55 pages).
Busby et al., "Multi-Layer Stack with Embedded Tamper-Detect Protection", U.S. Appl. No. 15/053,336, filed Feb. 25, 2016 (68 pages).
Campbell et al., "Tamper-Proof Electronic Packages With Two-Phase Dielectric Fluid", U.S. Appl. No. 15/139,503, filed Apr. 27, 2016 (60 pages).
Busby et al., "Tamper-Proof Electronic Packages Formed With Stressed Glass", U.S. Appl. No. 15/154,077, filed May 13, 2016 (45 pages).
Busby et al., "Tamper-Proof Electronic Packages With Stressed Glass Component Substrate(s)", U.S. Appl. No. 15/154,088, filed May 13, 2016 (56 pages).
Brodsky et al., "Circuit Layouts of Tamper-Respondent Sensors", U.S. Appl. No. 15/187,002, filed Jun. 20, 2016 (110 pages).
Brodsky et al., "Tamper-Respondent Assemblies with Enclosure-to-Board Protection", U.S. Appl. No. 15/193,525, filed Jun. 27, 2016 (54 pages).
Fisher et al., "Applying Pressure to Adhesive Using CTE Mismatch Between Components", U.S. Appl. No. 15/193,556, filed Jun. 27, 2016 (71 pages).
Busby et al., "Tamper-Respondent Assembly with Nonlinearity Monitoring", U.S. Appl. No. 15/194,738, filed Jun. 28, 2016 (48 pages).
Dangler et al., "Tamper-Respondent Sensors with Formed Flexible Layer(s)", U.S. Appl. No. 15/249,663, filed Aug. 29, 2016 (109 pages).
Brodsky et al., "Overlapping, Discrete Tamper-Respondent Sensors", U.S. Appl. No. 15/249,671, filed Aug. 29, 2016 (109 pages).
Dangler et al., "Tamper-Respondent Assemblies with Region(s) of Increased Susceptibility to Damage", U.S. Appl. No. 15/249,676, filed Aug. 29, 2016 (110 pages).
Dragone et al., "Tamper-Respondent Assembly with Sensor Connection Adapter", U.S. Appl. No. 15/268,959, filed Sep. 19, 2016 (45 pages).
Dragone et al., "Vented Tamper-Respondent Assemblies", U.S. Appl. No. 15/275,748, filed Sep. 26, 2016 (53 pages).
Dragone et al., "List of IBM Patents and Patent Applications Treated as Related", U.S. Appl. No. 15/275,762, filed Sep. 26, 2016, dated Sep. 26, 2016 (2 pages).
Busby et al., "Tamper-Respondent Assemblies with Trace Regions of Increased Susceptibility to Breaking", U.S. Appl. No. 15/341,108, filed Nov. 2, 2016 (56 pages).
Brodsky et al., "Enclosure with Inner Tamper-Respondent Sensor(s)", U.S. Appl. No. 15/409,851, filed Jan. 19, 2017 (115 pages).
Brodsky et al., "Tamper-Respondent Assemblies with Enclosure-to-Board Protection", U.S. Appl. No. 15/423,833, filed Feb. 3, 2017 (54 pages).

\* cited by examiner

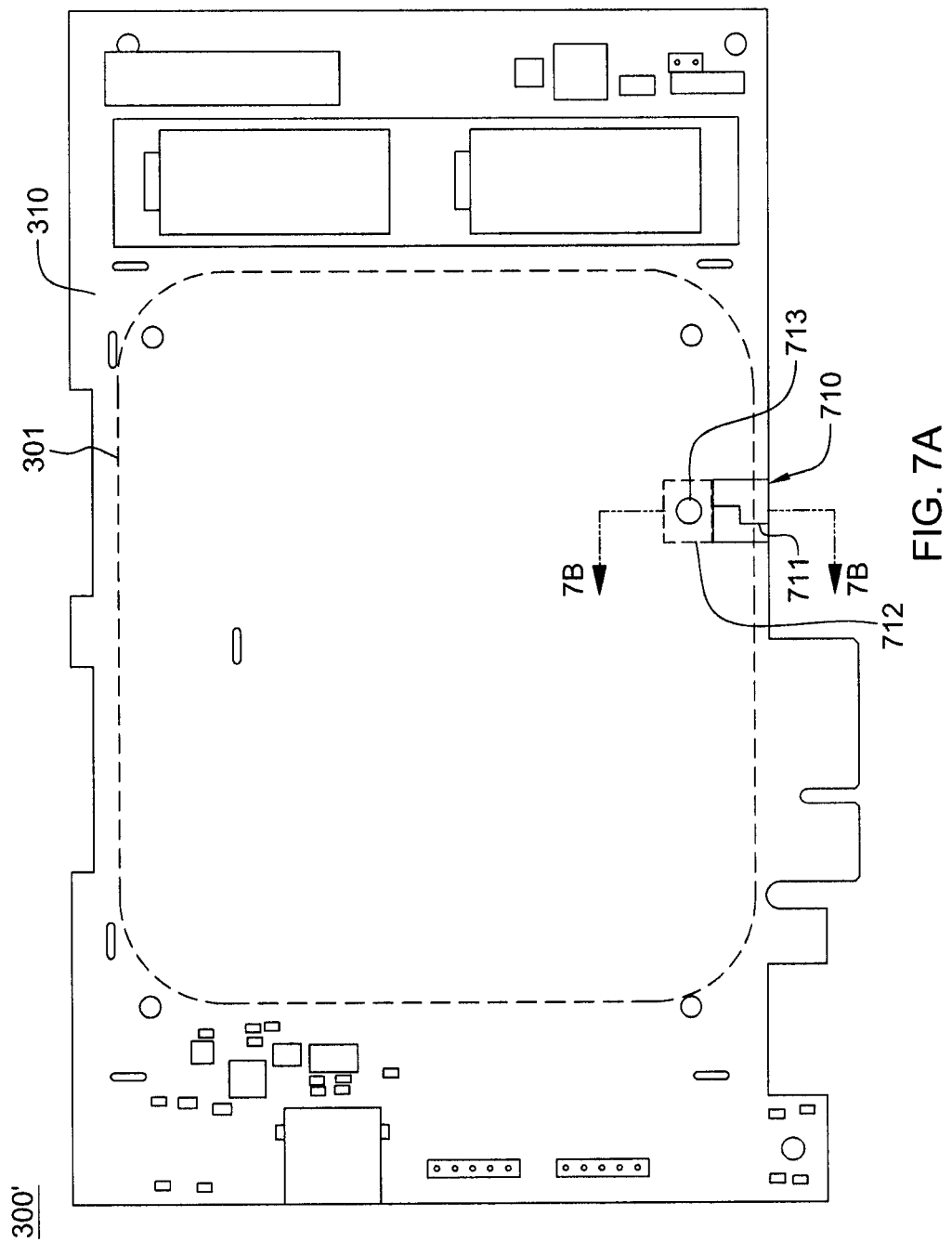

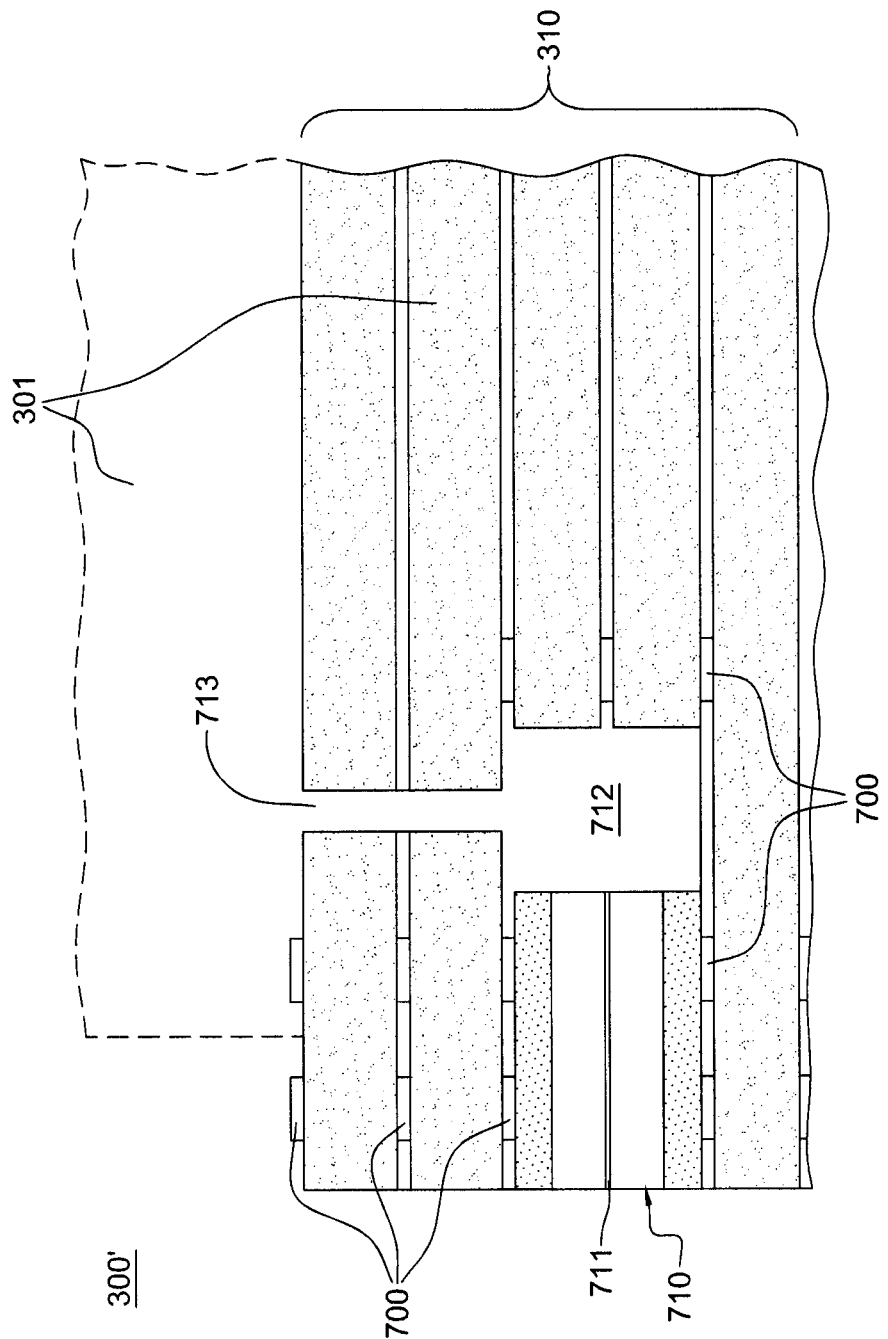

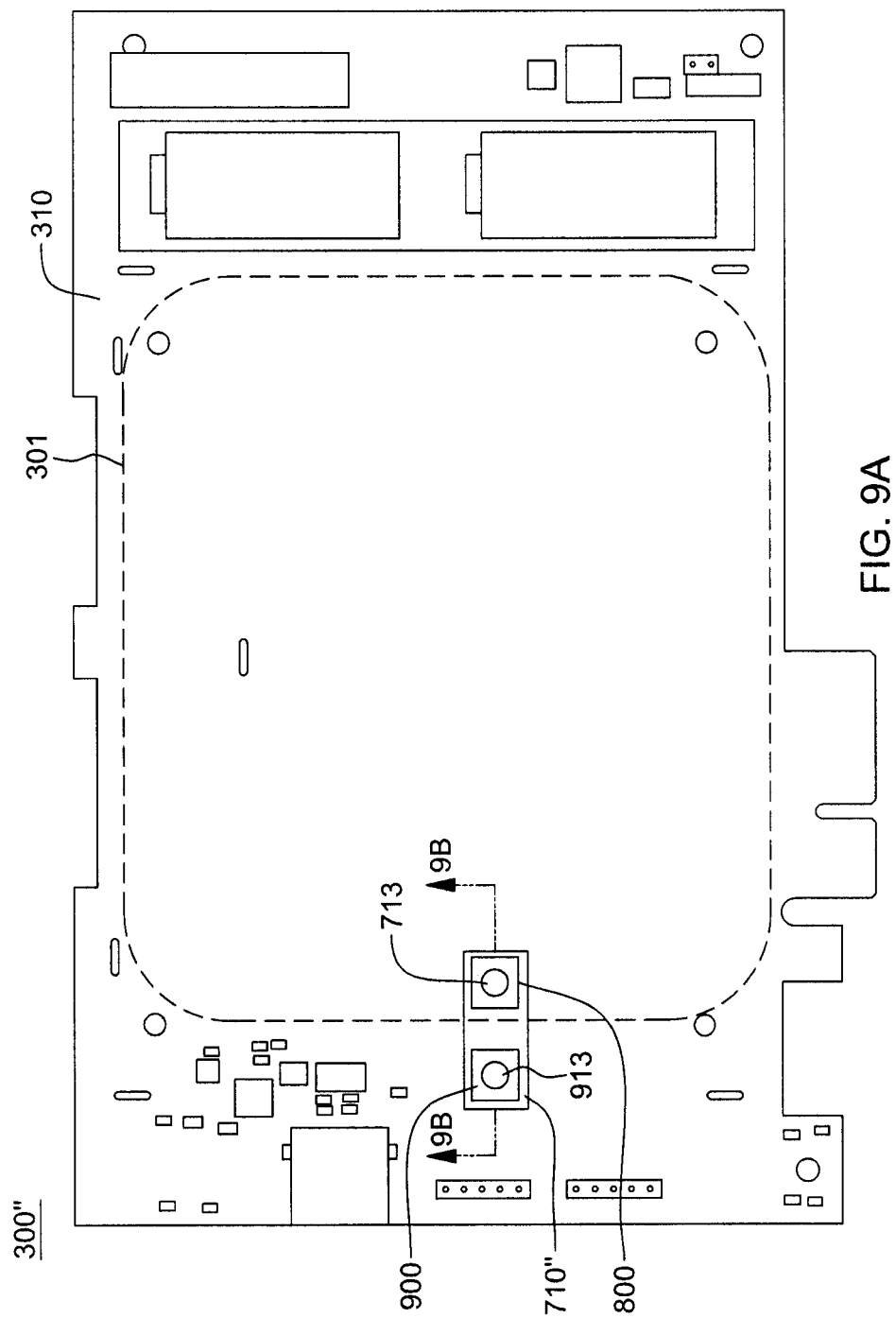

TAMPER-RESPONDENT ASSEMBLIES WITH IN SITU VENT STRUCTURE(S)

BACKGROUND

Many activities require secure electronic communications. To facilitate secure electronic communications, an encryption/decryption system may be implemented on an electronic assembly or printed circuit board assembly that is included in equipment connected to a communications network. Such an electronic assembly is an enticing target for malefactors since it may contain codes or keys to decrypt intercepted messages, or to encode fraudulent messages. To prevent this, an electronic assembly may be mounted in an enclosure, which is then wrapped in a security sensor and encapsulated with polyurethane resin. A security sensor may be, in one or more embodiments, a web or sheet of insulating material with circuit elements, such as closely-spaced, conductive lines fabricated on it. The circuit elements are disrupted if the sensor is torn, and the tear can be sensed in order to generate an alarm signal. The alarm signal may be conveyed to a monitor circuit in order to reveal an attack on the integrity of the assembly. The alarm signal may also trigger an erasure of encryption/decryption keys stored within the electronic assembly.

SUMMARY

Provided herein, in one or more aspects, is a tamper-respondent assembly which includes: a multilayer circuit board; a tamper-detection sensor embedded within the multilayer circuit board, the tamper-detection sensor defining, at least in part, a secure volume associated with the multilayer circuit board; and an in situ vent structure within the multilayer circuit board, the in situ vent structure including at least one vent channel, the at least one vent channel being in fluid communication with a space within the secure volume to facilitate venting the space of the secure volume.

In one or more other aspects, a tamper-respondent assembly is provided which includes: a multilayer circuit board; a tamper-detection sensor embedded within the multilayer circuit board, the tamper-detection sensor defining, at least in part, a secure volume associated with the multilayer circuit board; at least one electronic component disposed within a space within the secure volume; and an in situ vent structure within the multilayer circuit board, the in situ vent structure including at least one vent channel, the at least one vent channel being in fluid communication with the space within the secure volume to facilitate venting the space of the secure volume.

In one or more further aspects, a fabrication method is provided which includes fabricating a tamper-respondent assembly. The fabricating of the tamper-respondent assembly includes: providing a multilayer circuit board; providing a tamper-detection sensor embedded within the multilayer circuit board, the tamper-detection sensor defining, at least in part, a secure volume associated with the multilayer circuit board; and forming in place an in situ vent structure within the multilayer circuit board, the in situ vent structure including at least one vent channel, the at least one vent channel being in fluid communication with a space within the secure volume to facilitate venting the space of the secure volume.

Additional features and advantages are realized through the techniques of the present invention. Other embodiments and aspects of the invention are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

FIG. 7A is a plan view of one embodiment of a multilayer circuit board of a tamper-respondent assembly with an incorporated vent structure, in accordance with one or more aspects of the present invention;

FIG. 7B is a cross-sectional elevational view of the multilayer circuit board and vent structure of FIG. 7A, taken along line 7B-7B thereof, in accordance with one or more aspects of the present invention;

FIG. 9A is a further embodiment of a multilayer circuit board of a tamper-respondent assembly with an incorporated vent structure, in accordance with one or more aspects of the present invention;

DETAILED DESCRIPTION

Aspects of the present invention and certain features, advantages, and details thereof, are explained more fully below with reference to the non-limiting example(s) illustrated in the accompanying drawings. Descriptions of well-known materials, fabrication tools, processing techniques, etc., are omitted so as not to unnecessarily obscure the invention in detail. It should be understood, however, that the detailed description and the specific example(s), while indicating aspects of the invention, are given by way of illustration only, and are not by way of limitation. Various substitutions, modifications, additions, and/or arrangements, within the spirit and/or scope of the underlying inventive concepts will be apparent to those skilled in the art for this disclosure. Note further that reference is made below to the drawings, which are not drawn to scale for ease of understanding, wherein the same reference numbers used throughout different figures designate the same or similar components. Also, note that numerous inventive aspects and features are disclosed herein, and unless otherwise inconsistent, each disclosed aspect or feature is combinable with any other disclosed aspect or feature as desired for a particular application, for instance, for establishing a vented, secure volume about an electronic component(s) or electronic assembly to be protected.

Figure 1:
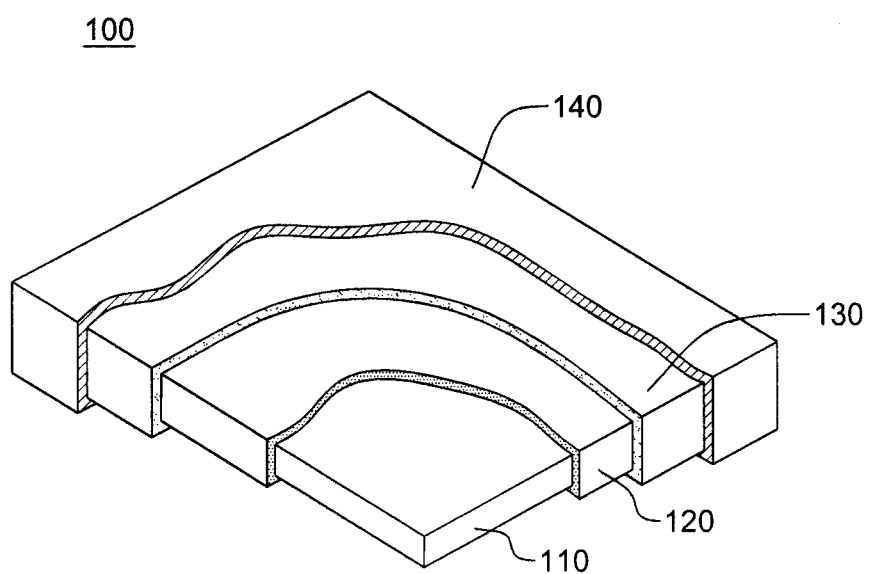
FIG. 1 is a partial cut-away of one embodiment of a tamper-proof electronic package.

Reference is first made to FIG. 1, which illustrates one approach for an electronic package 100 configured as a tamper-proof electronic package for purposes of discussion. In the depicted embodiment, an electronic assembly enclosure 110 is provided containing, for instance, an electronic assembly, which in one embodiment may include a plurality of electronic components, such as an encryption and/or decryption module and associated memory. The encryption and/or decryption module may comprise security-sensitive information with, for instance, access to the information stored in the module requiring use of a variable key, and with the nature of the key being stored in the associated memory within the enclosure.

In one or more implementations, a tamper-proof electronic package or tamper-respondent assembly, such as depicted, is configured or arranged to detect attempts to tamper with or penetrate into electronic assembly enclosure 110. Accordingly, electronic assembly enclosure 110 also includes, for instance, a monitor circuit which, if tampering is detected, activates an erase circuit to erase information stored within the associated memory, as well as the encryption and/or decryption module within the communications card. These components may be mounted on, and interconnected by, a multilayer circuit board, such as a printed circuit board or other multilayer substrate, and be internally or externally powered via a power supply provided within the electronic assembly enclosure.

In the embodiment illustrated, and as one example only, electronic assembly enclosure 110 may be surrounded by a tamper-detection sensor 120, an encapsulant 130, and an outer, thermally conductive enclosure 140. In one or more implementations, tamper-detection sensor 120 may include a tamper-detection laminate that is folded around electronic assembly enclosure 110, and encapsulant 130 may be provided in the form of a molding. Tamper-detection sensor 120 may include various detection layers, which are monitored through, for instance, a ribbon cable by the enclosure monitor, against attempts to penetrate enclosure 110 and damage the enclosure monitor or erase circuit, before information can be erased from the encryption module. The tamper-detection sensor may be, for example, any such article commercially available or described in various publications and issued patents, or any enhanced article such as disclosed herein.

By way of example, tamper-detection sensor 120 may be formed as a tamper-detection laminate comprising a number of separate layers with, for instance, an outermost lamination-detection layer including a matrix of, for example, diagonally-extending or sinusoidally-extending, conductive or semi-conductive lines printed onto a regular, thin insulating film. The matrix of lines forms a number of continuous conductors which would be broken if attempts are made to penetrate the film. The lines may be formed, for instance, by printing conductive traces onto the film and selectively connecting the lines on each side, by conductive vias, near the edges of the film. Connections between the lines and an enclosure monitor of the communications card may be provided via, for instance, one or more ribbon cables. The ribbon cable itself may be formed of lines of conductive material printed onto an extension of the film, if desired. Connections between the matrix and the ribbon cable may be made via connectors formed on one edge of the film. As noted, the laminate may be wrapped around the electronic assembly enclosure to define the tamper-detection sensor 120 surrounding enclosure 110.

In one or more implementations, the various elements of the laminate may be adhered together and wrapped around enclosure 110, in a similar manner to gift-wrapping a parcel, to define the tamper-detection sensor shape 120. The assembly may be placed in a mold which is then filled with, for instance, cold-pour polyurethane, and the polyurethane may be cured and hardened to form an encapsulant 130. The encapsulant may, in one or more embodiments, completely surround the tamper-detection sensor 120 and enclosure 110, and thus form a complete environmental seal, protecting the interior of the enclosure. The hardened polyurethane is resilient and increases robustness of the electronic package in normal use. Outer, thermally conductive enclosure 140 may optionally be provided over encapsulant 130 to, for instance, provide further structural rigidity to the electronic package.

When considering tamper-proof packaging, the electronic package needs to maintain defined tamper-proof requirements, such as those set forth in the National Institutes of Standards and Technology (NIST) Publication FIPS 140-2, which is a U.S. Government Computer Security Standard, used to accredit cryptographic modules. The NIST FIPS 140-2 defines four levels of security, named Level 1 to Level 4, with Security Level 1 providing the lowest level of security, and Security Level 4 providing the highest level of security. At Security Level 4, physical security mechanisms are provided to establish a complete envelope of protection around the cryptographic module, with the intent of detecting and responding to any unauthorized attempt at physical access. Penetration of the cryptographic module enclosure from any direction has a very high probability of being detected, resulting in the immediate zeroization of all plain text critical security parameters (CSPs). Security Level 4 cryptographic modules are useful for operation in physically unprotected environments. Security Level 4 also protects a cryptographic module against a security compromise due to environmental conditions or fluctuations outside the module's normal operating ranges for voltage and temperature. Intentional excursions beyond the normal operating ranges may be used by an attacker to thwart the cryptographic module's defenses. The cryptographic module is required to either include specialized environmental protection features designed to detect fluctuations and zeroize, critical security parameters, or to undergo rigorous environmental failure testing to provide reasonable assurances that the module will not be affected by fluctuations outside the normal operating range in a manner than can compromise the security of the module.

To address the demands for ever-improving anti-intrusion technology, and the higher-performance encryption/decryption functions being provided, enhancements to the tamper-proof, tamper-evident packaging for the electronic component(s) or assembly at issue are desired.

Numerous enhancements are described herein to, for instance, tamper-proof electronic packages or tamper-respondent assemblies. As noted, the numerous inventive aspects described herein may be used singly, or in any desired combination. Additionally, in one or more implementations, the enhancements described herein may be provided to work within defined space limitations for existing packages.

Disclosed hereinbelow with reference to FIGS. 2-15 are various approaches and/or enhancements to creating, for instance, a secure volume for accommodating one or more electronic components, such as one or more encryption and/or decryption modules and associated components of, for instance, a communications card or other electronic assembly to be protected.

Figure 2:
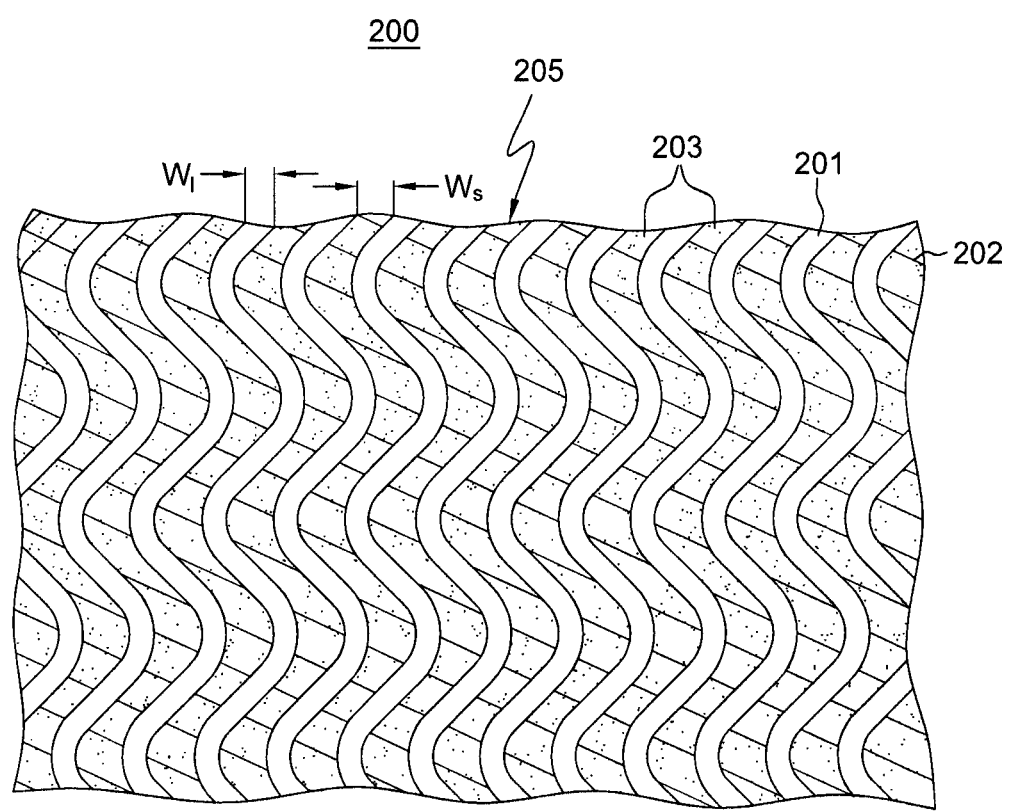
FIG. 2 depicts one embodiment of a tamper-detection sensor with conductive lines forming, at least in part, at least one tamper-detect network, in accordance with one or more aspects of the present invention.

FIG. 2 depicts a portion of one embodiment of a tamper-detection layer 205 (or laser and pierce-respondent layer) of a tamper-detection sensor 200 or security sensor, such as discussed herein. In FIG. 2, tamper-detection layer 205 includes circuit lines or traces 201 provided on one or both opposite sides of a flexible layer 202, which in one or more embodiments, may be a flexible insulating layer or film. FIG. 2 illustrates circuit lines 201 on, for instance, one side of flexible layer 202, with the traces on the opposite side of the film being, for instance, the same pattern, but (in one or more embodiments) offset to lie directly below spaces 203, between circuit lines 201. As described below, the circuit lines on one side of the flexible layer may be of a line width $W_l$ and have a pitch or line-to-line spacing $W_s$ such that piercing of the layer 205 at any point results in damage to at least one of the circuit lines traces 201. In one or more implementations, the circuit lines may be electrically connected in-series or parallel to define one or more conductors which may be electrically connected in a network to an enclosure monitor, which may, in one or more implementations, monitor the resistance of the lines. Detection of an increase, or other change, in resistance, caused by cutting or damaging one of the traces, will cause information within the encryption and/or decryption module to be erased. Providing conductive lines 201 in a pattern, such as a sinusoidal pattern, may advantageously make it more difficult to breach tamper-detection layer 205 without detection. Note, in this regard, that conductive lines 201 could be provided in any desired pattern. For instance, in an alternate implementation, conductive lines 201 could be provided as parallel, straight conductive lines, if desired, and the pattern or orientation of the pattern may vary between sides of a layer, and/or between layers.

As noted, as intrusion technology continues to evolve, anti-intrusion technology needs to continue to improve to stay ahead. In one or more implementations, the above-summarized tamper-detection sensor 200 of FIG. 2 may be disposed over an outer surface of an electronic enclosure, such as an electronic enclosure described above in connection with FIG. 1. Alternatively, as described further herein, the tamper-detection sensor may cover or line an inner surface of an electronic enclosure to provide a secure volume about at least one electronic component to be protected. Still further, the tamper-detection sensor, or more particularly, the tamper-detect circuit(s) of the sensor, could be embedded within a multilayer circuit board described below.

In one or more aspects, disclosed herein is a tamper-detection sensor 200 with circuit lines 201 having reduced line widths $W_l$ of, for instance, 200 µm, or less, such as less than or equal to 100 µm, or even more particularly, in the range of 30-70 µm. This is contrasted with conventional trace widths, which are typically on the order of 250 µm or larger. Commensurate with reducing the circuit line width $W_l$, line-to-line spacing width $W_s$ 203 is also reduced to less than or equal to 200 µm, such as less than or equal to 100 µm, or for instance, in a range of 30-70 µm. Advantageously, by reducing the line width $W_l$ and line-to-line spacing $W_s$ of circuit lines 201 within tamper-detection sensor 200, the circuit line width and pitch is on the same order of magnitude as the smallest intrusion instruments currently available, and therefore, any intrusion attempt will necessarily remove a sufficient amount of a circuit line(s) to cause resistance to change, and thereby the tamper intrusion to be detected. Note that, by making the circuit line width of the smaller dimensions disclosed herein, any cutting or damage to the smaller-dimensioned circuit line will also be more likely to be detected, that is, due to a greater change in resistance. For instance, if an intrusion attempt cuts a 100 μm width line, it is more likely to reduce the line width sufficiently to detect the intrusion by a change in resistance. A change in a narrower line width is more likely to result in a detectable change in resistance, compared with, for instance, a 50% reduction in a more conventional line width of 350 μm to, for instance, 175 μm. The smaller the conductive circuit line width becomes, the more likely that a tampering of that line will be detected.

Note also that a variety of materials may advantageously be employed to form the circuit lines when implemented using resistance monitoring. For instance, the circuit lines may be formed of a conductive ink (such as a carbon-loaded conductive ink) printed onto one or both opposite sides of one or more of the flexible layers 202 in a stack of such layers. Alternatively, a metal or metal alloy could be used to form the circuit lines, such as copper, silver, intrinsically conductive polymers, carbon ink, or nickel-phosphorus (NiP), such as Omega-Ply®, offered by Omega Technologies, Inc. of Culver City, Calif. (USA), or nickel-chrome, such as Ticer™ offered by Ticer Technologies, Chandler, Ariz. (USA). Note that the process employed to form the fine circuit lines or traces on the order described herein is dependent, in part, on the choice of material used for the circuit lines. For instance, if copper circuit lines are being fabricated, then additive processing, such as plating up copper traces, or subtractive processing, such as etching away unwanted copper between trace lines, may be employed. By way of further example, if conductive ink is employed as the circuit line material, fine circuit lines on the order disclosed herein can be achieved by focusing on the rheological properties of the conductive ink formulation. Further, rather than simple pneumatics of pushing conductive ink through an aperture in a stencil with a squeegee, the screen emulsion may be characterized as very thin (for instance, 150 to 200 μm), and a squeegee angle may be used such that the ink is sheared to achieve conductive ink breakaway rather than pumping the conductive ink through the screen apertures. Note that the screen for fine line width printing such as described herein may have the following characteristics in one specific embodiment: a fine polyester thread for both warp and weave on the order of 75 micrometers; a thread count between 250-320 threads per inch; a mesh thickness of, for instance, 150 micrometers; an open area between threads that is at least 1.5× to 2.0× the conductive ink particle size; and to maintain dimensional stability of the print, the screen snap-off is kept to a minimum due the screen strain during squeegee passage.

In a further aspect, the flexible layer 202 itself may be further reduced in thickness from a typical polyester layer by selecting a crystalline polymer to form the flexible layer or substrate. By way of example, the crystalline polymer could comprise polyvinylidene difluoride (PVDF), or Kapton, or other crystalline polymer material. Advantageously, use of a crystalline polymer as the substrate film may reduce thickness of the flexible layer 202 to, for instance, 2 mils thick from a more conventional amorphous polyester layer of, for instance, 5-6 mils. A crystalline polymer can be made much thinner, while still maintaining structural integrity of the flexible substrate, which advantageously allows for far more folding, and greater reliability of the sensor after folding. Note that the radius of any fold or curvature of the sensor is necessarily constrained by the thickness of the layers comprising the sensor. Thus, by reducing the flexible layer thickness to, for instance, 2 mils, then in a four tamper-detection layer stack, the stack thickness can be reduced from, for instance, 20 mils in the case of a typical polyester film, to 10 mils or less with the use of crystalline polymer films.

Figure 3A:
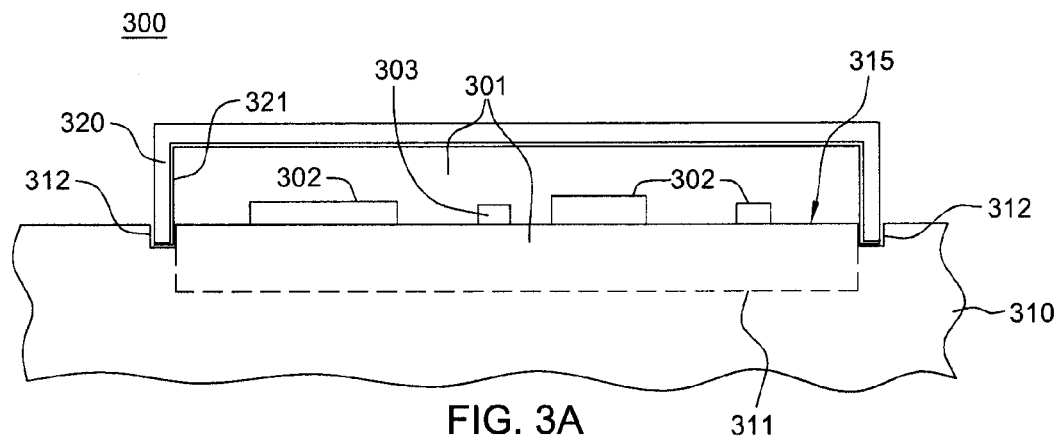
FIG. 3A is a cross-sectional elevational view of another embodiment of a tamper-proof electronic package, or tamper-respondent assembly, which includes (in part) an enclosure, and a multilayer circuit board with an embedded tamper-detection sensor, in accordance with one or more aspects of the present invention.
Figure 3B:
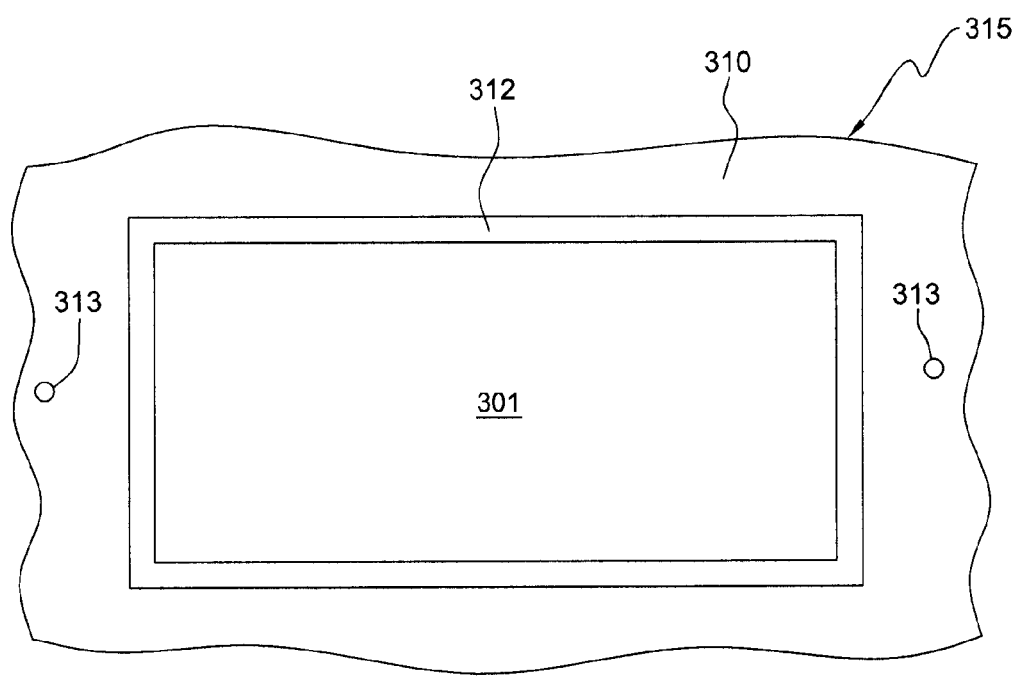
FIG. 3B is a top plan view of the multilayer circuit board of FIG. 3A, depicting one embodiment of the secure volume defined, in part, within the multilayer circuit board, in accordance with one or more aspects of the present invention.

FIGS. 3A & 3B depict one embodiment of a tamper-proof electronic package 300, or tamper-respondent assembly, which comprises one or more electronic components, such as a circuit 315 and/or electronic devices (or elements) 302 to be protected, in accordance with one or more further aspects of the present invention.

Referring collectively to FIGS. 3A & 3B, circuit 315 resides on or is embedded within a multilayer circuit board 310, which also has an embedded tamper-detection sensor 311 that facilitates defining, in part, a secure volume 301 associated with multilayer circuit board 310 that (in one or more embodiments) extends into multilayer circuit board 310. In particular, in the embodiment of FIGS. 3A & 3B, secure volume 301 may exist partially within multilayer circuit board 310, and partially above multilayer circuit board 310. One or more electronic devices 302 are mounted to multilayer circuit board 310 within secure volume 301 and may comprise, for instance, one or more encryption modules and/or decryption modules, and/or associated components, to be protected within the tamper-proof electronic package. In one or more implementations, the one or more electronic components to be protected may comprise, for instance, a secure communications card of a computer system.

Tamper-proof electronic package 300 further includes an enclosure 320, such as a pedestal-type enclosure, mounted to multilayer circuit board 310 within, for instance, a continuous groove (or trench) 312 formed within an upper surface of multilayer circuit board 310, and secured to the multilayer circuit board 310 via, for instance, a structural adhesive disposed within continuous groove 312. In one or more embodiments, enclosure 320 may comprise a thermally conductive material and operate as a heat sink for facilitating cooling of the one or more electronic components 302 within the secure volume. A security mesh or tamper-detection sensor 321 may be associated with enclosure 320, for example, wrapping around the inner surface of enclosure 320, to facilitate defining, in combination with tamper-detection sensor 311 embedded within multilayer circuit board 310, secure volume 301. In one or more implementations, tamper-detection sensor 321 may extend down into continuous groove 312 in multilayer circuit board 310 and may, for instance, even wrap partially or fully around the lower edge of enclosure 320 within continuous groove 312 to provide enhanced tamper detection where enclosure 320 couples to multilayer circuit board 310. In one or more implementations, enclosure 320 may be securely affixed to multilayer circuit board 310 using, for instance, a bonding material such as an epoxy or other adhesive.

Briefly described, tamper-detection sensor 321 may comprise, in one or more examples, one or more tamper-detection layers which include circuit lines or traces provided on one or both sides of a flexible layer, which in one or more implementations, may be a flexible insulating layer or film. The circuit lines on one or both sides of the flexible layer may be of a line width and have a pitch or line-to-line spacing such that piercing of the layer at any point results in damage to one or more of the circuit lines or traces. In one or more implementations, the circuit lines may define one or more conductors which may be electrically connected in a network to an enclosure monitor or detector 303, which monitors, for instance, resistance on the lines, or as described below, in the case of conductors, may monitor for a nonlinearity, or non-linear conductivity change, on the conductive lines. Detection of a change in resistance or a nonlinearity caused by cutting or damaging one or more of the lines, will cause information within the secure volume to be automatically erased. The conductive lines of the tamper-detection sensor may be in any desired pattern, such as a sinusoidal pattern, to make it more difficult to breach the tamper-detection layer without detection.

For resistive monitoring, a variety of materials may be employed to form the circuit lines. For instance, the circuit lines may be formed of a metal or metal alloy, such as copper, or silver, or could be formed, for example, of an intrinsically-conductive polymer, carbon ink, or nickel phosphorous (NiP), or Omega-Ply®, offered by Omega Technologies, Inc., of Culver City, Calif. (USA), or Ticer™, offered by Ticer Technologies, Chandler, Ariz. (USA). The process employed to form the fine circuit lines or traces is dependent, in part, on the choice of materials used for the circuit lines. For instance, if copper circuit lines are fabricated, then additive processing, such as plating of copper traces, or subtractive processing, such as etching away unwanted copper between trace lines, may be employed.

As noted, in one or more implementations, the circuit lines of the tamper-detection sensor(s) lining the inner surface(s) of enclosure 320, or even printed directly onto one or more layers formed over the inner surface of enclosure 320, may be connected to define one or more detect networks.

If a flexible layer is used over the inner surface of enclosure 320, then the flexible layer may be formed of a crystalline polymer material. For instance, the crystalline polymer could comprise polyvinylidene difluoride (PVDF), or Kapton, or other crystalline polymer material. Advantageously, a crystalline polymer may be made much thinner, while still maintaining structural integrity of the flexible substrate, which also allows for enhanced folding, and greater reliability of the sensor after folding.

As depicted in FIG. 3B, one or more external circuit connection vias 313 may be provided within multilayer circuit board 310 for electrically connecting to the one or more electronic components within secure volume 301. These one or more external circuit connection vias 313 may electrically connect to one or more external signal lines or planes (not shown) embedded within multilayer circuit board 310 and extending, for instance, into a secure base region of (or below) secure volume 301, as explained further below. Electrical connections to and from secure volume 301 may be provided by coupling to such external signal lines or planes within the multilayer circuit board 310.

As noted, secure volume 301 may be sized to house one or more electronic components to be protected, and may be constructed to extend into multilayer circuit board 310. In one or more implementations, multilayer circuit board 310 includes electrical interconnect within the secure volume 301 defined in the board, for instance, for electrically connecting one or more tamper-detection layers of the embedded tamper-detection sensor 311 to associated monitor circuitry also disposed within secure volume 301, along with, for instance, one or more daughter cards, such as memory DIMMs, PCIe cards, processor cards, etc.

Note that the packaging embodiment depicted in FIGS. 3A & 3B is presented by way of example only. Other configurations of enclosure 320, or multilayer circuit board 310 may be employed, and/or other approaches to coupling enclosure 320 and multilayer circuit board 310 may be used.

For instance, in one or more alternate implementations, enclosure 320 may be securely affixed to an upper surface of multilayer circuit board 310 (without a continuous groove) using, for instance, a structural bonding material such as an epoxy or other adhesive.

Figure 4:
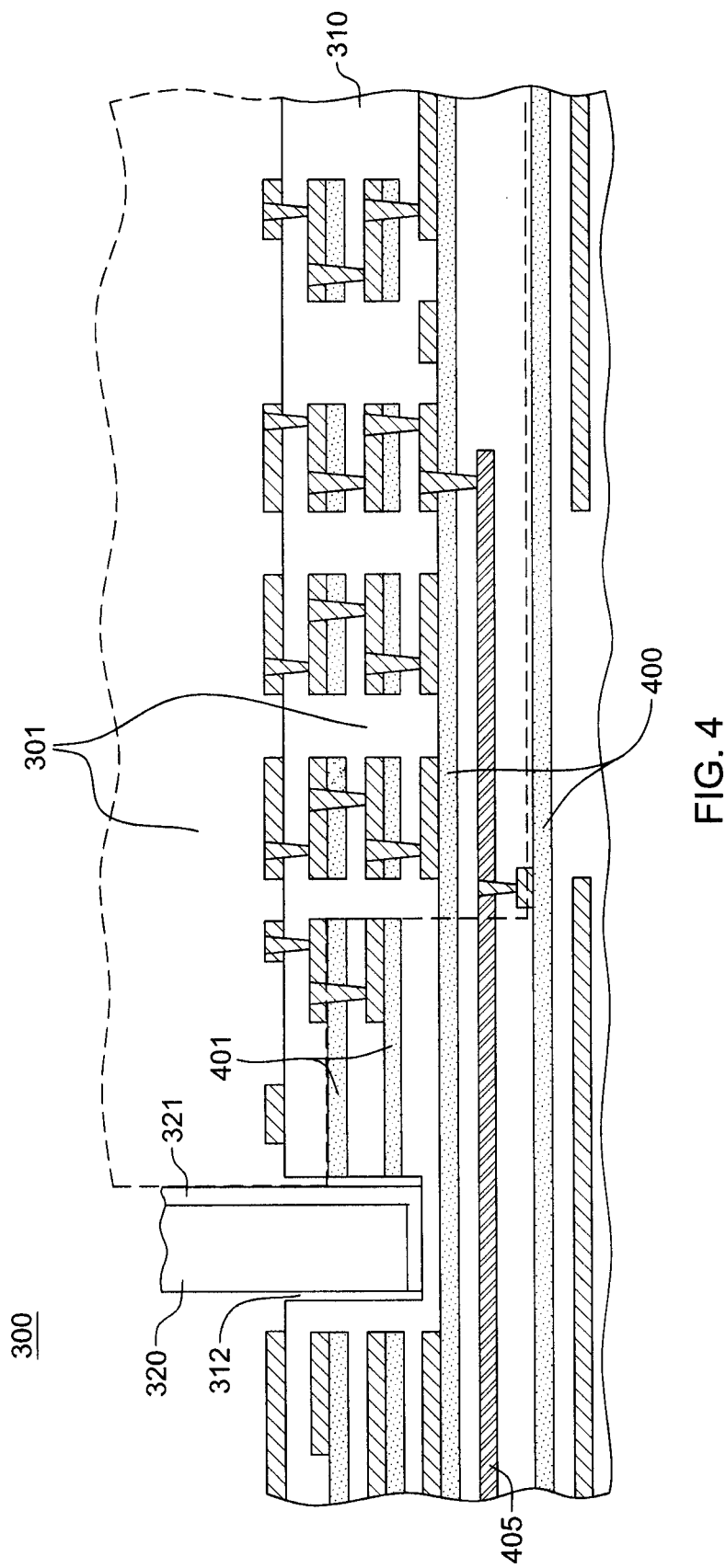
FIG. 4 is a partial cross-sectional elevational view of a more detailed embodiment of the tamper-respondent assembly of FIGS. 3A & 3B comprising (in part) an enclosure and a multilayer circuit board with embedded tamper-detection sensor, in accordance with one or more aspects of the present invention.

By way of further example, FIG. 4 depicts a partial cross-sectional elevational view of a more detailed embodiment of tamper-proof electronic package 300, and in particular, of multilayer circuit board 310, to which enclosure 320 is secured. In this configuration, the embedded tamper-detection sensor includes multiple tamper-detection layers including, by way of example, at least one tamper-detection mat (or base) layer 400, and at least one tamper-detection frame 401. In the example depicted, two tamper-detection mat layers 400 and two tamper-detection frames 401 are illustrated, by way of example only. The lower-most tamper-detection mat layer 400 may be a continuous sense or detect layer extending completely below the secure volume being defined within and/or above multilayer circuit board 310. One or both tamper-detection mat layers 400 below secure volume 301 may be partitioned into multiple circuit zones. Within each tamper-detection mat layer, or more particularly, within each circuit zone of each tamper-detection mat layer, multiple circuits or conductive traces may be provided in any desired configuration. Further, the conductive traces within the tamper-detection layers may be implemented as, for instance, a resistive layer.

As illustrated, one or more external signal lines or planes 405 may enter secure volume 301 between, in one embodiment, two tamper-detection mat layers 400, and then electrically connect upwards into the secure volume 301 through one or more conductive vias, arranged in any desired location and pattern. In the configuration depicted, the one or more tamper-detection frames 401 are disposed at least inside of the area defined by continuous groove 312 accommodating the base of enclosure 320. Together with the tamper-detection sensor(s) 321 associated with enclosure 320, tamper-detection frames 401, and tamper-detection mat layers 400, define secure volume 301, which may extend, in part, into multilayer circuit board 310. With secure volume 301 defined, in part, within multilayer circuit board 310, the external signal line(s) 405 may be securely electrically connected to, for instance, the one or more electronic components mounted to, or of, multilayer circuit board 310 within secure volume 301. In addition, secure volume 301 may accommodate electrical interconnection of the conductive traces of the multiple tamper-detection layers 400, 401, for instance, via appropriate monitor circuitry.

Added security may be provided by extending tamper-detection mat layers 400 (and if desired, tamper-detection frames 401) outward past the periphery of enclosure 320. In this manner, a line of attack may be made more difficult at the interface between enclosure 320 and multilayer circuit board 310 since the attack would need to clear, for instance, tamper-detection mat layers 400, the enclosure 320, as well as the tamper-detection frames 401 of the embedded tamper-detection sensor.

Numerous variations on multilayer circuit board 310 of FIGS. 3A-4 are possible. For instance, in one embodiment, the embedded tamper-detection sensor may include one or more tamper-detection mat layers 400 and one or more tamper-detection frames 401, such as described above, and a tri-plate structure comprising one or more external signal lines or layers sandwiched between an upper ground plane and a lower ground plane. In this configuration, high-speed transfer of signals to and from the secure volume, and in particular, to and from the one or more electronic components resident within the secure volume, would be facilitated.

Note also that, once the secure volume is defined in part within multilayer circuit board 310, conductive vias within the secure volume between layers of multilayer circuit board 310 may be either aligned, or offset, as desired, dependent upon the implementation. Alignment of conductive vias may facilitate, for instance, providing a shortest connection path, while offsetting conductive vias between layers may further enhance security of the tamper-proof electronic package by making an attack into the secure volume through or around one or more tamper-detection layers of the multiple tamper-detection layers more difficult.

The tamper-detection layers of the embedded tamper-detection sensor formed within the multilayer circuit board of the electronic circuit or electronic package may include multiple conductive traces or lines formed between, for instance, respective sets of input and output contacts or vias at the trace termination points. Any pattern and any number of conductive traces or circuits may be employed in defining a tamper-detection layer or a tamper-detection circuit zone within a tamper-detection layer. For instance, 4, 6, 8, etc., conductive traces may be formed in parallel (or otherwise) within a given tamper-detection layer or circuit zone between the respective sets of input and output contacts to those conductive traces.

Figure 5:
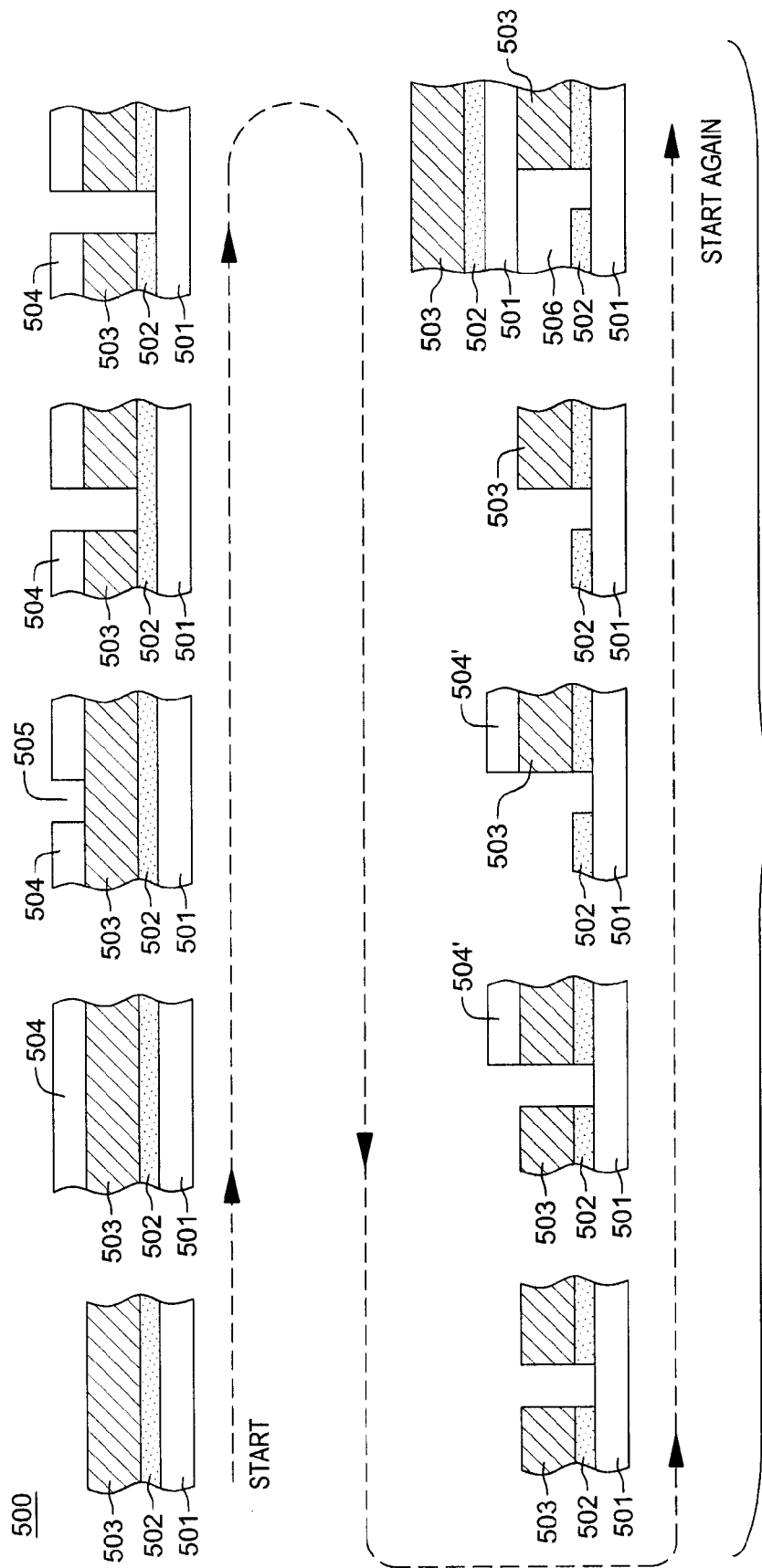
FIG. 5 depicts one embodiment of a process of fabricating a multilayer circuit board with an embedded tamper-detection sensor, in accordance with one or more aspects of the present invention.

In one or more implementations, the multilayer circuit board may be a multilayer wiring board or printed circuit board formed, for instance, by building up the multiple layers of the board. FIG. 5 illustrates one embodiment for forming and patterning a tamper-detection layer within such a multilayer circuit board.

As illustrated in FIG. 5, in one or more implementations, a tamper-detection layer, such as a tamper-detection mat layer or a tamper-detection frame disclosed herein, may be formed by providing a material stack comprising, at least in part, a structural layer 501, such as a pre-preg (or pre-impregnated) material layer, a trace material layer 502 for use in defining the desired trace patterns, and an overlying conductive material layer 503, to be patterned to define conductive contacts or vias electrically connecting to the pattern of traces being formed within the trace material layer 502, for instance, at trace terminal points. In one or more implementations, the trace material layer 502 may comprise nickel phosphorous (NiP), and the overlying conductive layer 503 may comprise copper. Note that these materials are identified by way of example only, and that other trace and/or conductive materials may be used within the build-up 500.

A first photoresist 504 is provided over build-up 500, and patterned with one or more openings 505, through which the overlying conductive layer 503 may be etched. Depending on the materials employed, and the etch processes used, a second etch process may be desired to remove portions of trace material layer 502 to define the conductive traces of the subject tamper-detection layer. First photoresist 504 may then be removed, and a second photoresist 504' is provided over the conductive layer 503 features to remain, such as the input and output contacts. Exposed portions of conductive layer 503 are then etched, and the second photoresist 504' may be removed, with any opening in the layer being filled, for instance, with an adhesive (or pre-preg) 506 and a next build-up layer is provided, as shown. Note that in this implementation, most of overlying conductive layer 503 is etched away, with only the conductive contacts or vias remaining where desired, for instance, at the terminal points of the traces formed within the layer by the patterning of the trace material layer 502. Note that any of a variety of materials may be employed to form the conductive lines or traces within a tamper-detection layer. Nickel-phosphorous (NiP) is particularly advantageous as a material since it is resistant to contact by solder, or use of a conductive adhesive to bond to it, making it harder to bridge from one circuit or trace to the next during an attempt to penetrate into the protected secure volume of the electronic circuit. Other materials which could be employed include OhmegaPly®, offered by Ohmega Technologies, Inc., of Culver City, Calif. (USA), or Ticer™, offered by Ticer Technologies of Chandler, Ariz. (USA).

The trace lines or circuits within the tamper-detection layers, and in particular, the tamper-detection circuit zones, of the embedded tamper-detection sensor, along with the tamper detector monitoring the enclosure, may be electrically connected to detect or compare circuitry provided, for instance, within secure volume 301 (FIG. 3A) of the tamper-proof electronic package. The detect circuitry may include various bridges or compare circuits, and conventional printed wiring board electrical interconnect inside secure volume 301 (FIG. 3A), for instance, located within the secure volume defined by the tamper-detection frames 401 (FIG. 4), and the tamper-detection mat layers 400 (FIG. 4).

Note that advantageously, different tamper-detection circuit zones on different tamper-detection layers may be electrically interconnected into, for instance, the same detect circuitry. Thus, any of a large number of interconnect configurations may be possible. For instance, if each of two tamper-detection mat layers contains 30 tamper-detection circuit zones, and each of two tamper-detection frames contains 4 tamper-detection circuit zones, then, for instance, the resultant 68 tamper-detection circuit zones may be connected in any configuration within the secure volume to create the desired arrangement of circuit networks within the secure volume being monitored for changes in resistance or tampering. Note in this regard, that the power supply or battery for the tamper-detection sensor may be located internal or external to the secure volume, with the sensor being configured to trip and destroy any protected or critical data if the power supply or battery is tampered with.

Figure 6:
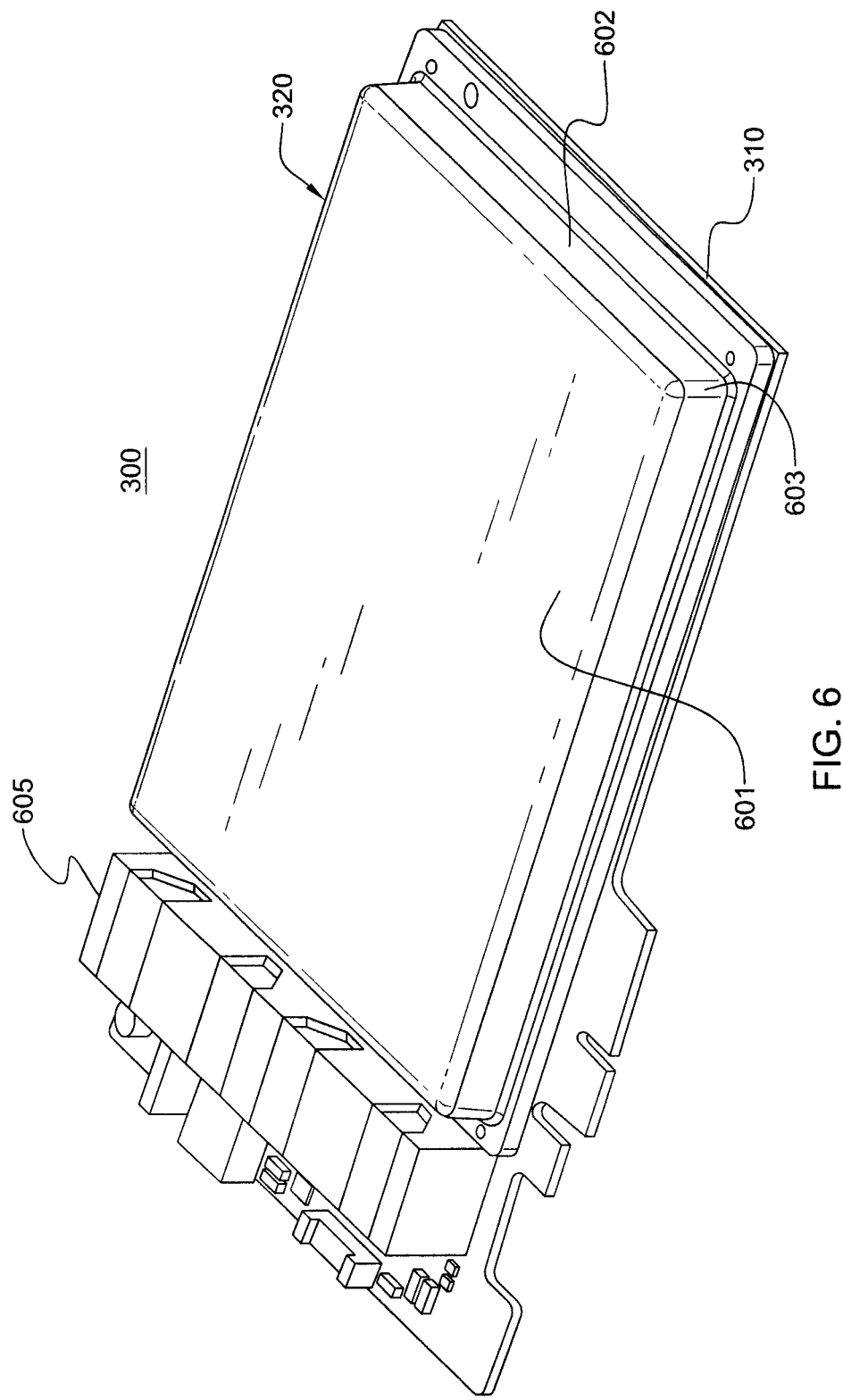
FIG. 6 is an isometric view of one embodiment of a tamper-respondent assembly, in accordance with one or more aspects of the present invention.

By way of further example, an isometric view of one embodiment of a tamper-proof electronic package 300 is depicted in FIG. 6, wherein an enclosure 320 is shown sealed to multilayer circuit board 310 to define a secure volume about one or more electronic components, as described herein. In the embodiment depicted, enclosure 320 may be formed of a thermally conductive material, and includes a main surface 601 and sidewall(s) 602 which include sidewall corners 603. An inner surface of enclosure 320 would include an inner main surface, and an inner sidewall surface corresponding to main surface 601 and sidewall(s) 602 respectively, with the inner main surface and inner sidewall surfaces being covered, at least in part, by one or more tamper-detection sensors, such as described above. A power supply 605 or battery for the tamper-detection sensor may be located, as depicted in this embodiment, external to the secure volume, with the tamper detector being configured to trip and destroy any protected or critical data if the power supply or battery is tampered with. Enclosure 320 may be adhered or mechanically affixed to multilayer circuit board 310, which as noted above, may include its own embedded tamper-detection sensor(s).

By way of further enhancement, disclosed herein are various vented, tamper-respondent assemblies and methods of fabrication. In particular, in one or more implementations, the tamper-respondent assembly may incorporate or include a vent structure within, for instance, a multilayer circuit board of the tamper-respondent assembly. The vent structure includes at least one vent channel in fluid communication with a space within the secure volume of the tamper-respondent assembly, and facilitates venting the space of the secure volume. The vent channel(s) may be, for instance, one or more air passages, which couple in fluid communication space within the secure volume of the assembly and an unsecure region or space external to the secure volume. Note that in this context, "in fluid communication" refers to air or gas communication being established between (for instance) the space within the secure volume provided by the tamper-respondent assembly and the at least one vent channel of the vent structure, which is also in fluid communication with the unsecured region external to the secure volume. Advantageously, in one or more implementations, the vent structure allows, in part, compensating for pressure differences between the space within the secure volume and the unsecured region external to the secure volume, such as ambient air about the tamper-respondent assembly. Additionally, the vented tamper-respondent assemblies disclosed herein advantageously provide enhanced security over other vented assemblies, and simplify the assembly process.

In general, provided herein are tamper-respondent assemblies and methods of fabrication which incorporate (for instance, laminate) a vent structure into a multilayer circuit board of the tamper-respondent assembly. In addition to the multilayer circuit board and the vent structure, the tamper-respondent assemblies include a tamper-detection sensor embedded within the multilayer circuit board. The tamper-detection sensor defines, at least in part, a secure volume associated with the multilayer circuit board. In implementation, the vent structure may include at least one vent channel, with the at least one vent channel being in fluid communication with a space within the secure volume to facilitate venting the space of the secure volume.

In one or more implementations, the tamper-respondent assembly further includes an enclosure coupled to the multilayer circuit board, such as adhesively secured to the circuit board. The enclosure encloses, at least in part, one or more electronic components to be protected. In addition, a tamper-detection sensor overlies or covers, at least in part, an inner surface of the enclosure. The tamper-detection sensor covering, at least in part, the inner surface of the enclosure and the embedded tamper-detection sensor within the multilayer circuit board together facilitate defining the secure volume, within which the electronic component(s) to be protected resides.

In one or more embodiments, the at least one vent channel of the vent structure may extend to an edge of the multilayer circuit board. Additionally, the multilayer circuit board may include at least one vent opening extending (for example, vertically) from a surface of the multilayer circuit board within the secure volume into the multilayer circuit board, with the at least one vent opening in the multilayer circuit board being in fluid communication with the at least one vent channel of the vent structure. For instance, the at least one vent opening may be at least one drill hole extending into the multilayer circuit board to be in fluid communication with the at least one vent channel of the vent structure.

In one or more implementations, the vent structure may further include a vent cavity located within the secure volume, such as an enlarged cavity. The vent cavity of the vent structure may facilitate coupling in fluid communication the at least one vent opening extending into the multilayer circuit board and the at least one vent channel of the vent structure. In certain implementations, the vent cavity within the vent structure may be a first vent cavity, and the at least one vent opening may be at least one first vent opening, with the vent structure further including a second vent cavity, the second vent cavity being located external to the secure volume, and the second vent cavity facilitating coupling in fluid communication at least one second vent opening extending, at least in part, into the multilayer circuit board and the at least one vent channel of the vent structure.

In one or more embodiments, the space of the secure volume in fluid communication with the at least one vent channel of the vent structure may be within the multilayer circuit board itself. Further, the secure volume may reside fully within the multilayer circuit board, and the space may accommodate one or more electronic components to be protected.

In one or more other implementations, the tamper-detection sensor embedded within the multilayer circuit board may include at least one tamper-detect network, and the vent structure may be formed, at least in part, of a conductive or resistive material and be electrically connected as part of the tamper-detect network(s) of the tamper-detection sensor. In this manner, an attempted intrusion event through the vent structure may result in a change in resistance within the detect network, and thus be detected by the monitor circuitry monitoring the tamper-detect network(s).

The vent structure may be implemented in a variety of configurations. For instance, the vent structure may be or include a thin, flat vent plate, which has the at least one vent channel. By way of example, the at least one vent channel may extend between opposing first and second ends of the vent plate, with (for instance) opposite main sides of the vent plate being substantially parallel. By way of example, the vent plate may be, in one or more implementations, a thin, multilayer vent plate formed of multiple layers, such as multiple metal layers, such as a base plate and a cover plate. By way of specific example, the multilayer vent plate may be a rigid, or semi-rigid structure, such as a metal, polymer, or plastic, etc., structure, with adjacent layers of the multilayer structure being strongly affixed together. For instance, where the vent plate is a metal structure, adjacent metal layers of the multilayer vent plate may be welded, soldered, and/or braised together.

In one or more embodiments, the at least one vent channel of the vent structure includes one or more directional changes of 90°, or greater in, for instance, a zigzag pattern. In one or more embodiments, the at least one vent channel may have a directional component in an opposite direction to a direction of the vent channel(s), before the directional change. Additionally, in one or more implementations, the at least one vent channel and vent structure may include multiple zigzag directional changes, with one or more of the directional changes having associated therewith a false, terminating passage, which extends within the vent structure, from the directional change(s) to make insertion of, for instance, a wire through the vent channel(s) difficult, if not impossible.

By way of specific example, the vent channel within the vent structure may be extremely small, with a characteristic dimension of (for instance) 0.1-0.2 mm, such as 0.15 mm, and may include multiple zigzag directional changes, which prohibit the insertion of a wire down the length of the vent channel(s). Further, the vent structure may be thin and flat to prevent drilling or other intrusions, that is, without protruding out through the vent structure and contacting one of the tamper-detect network layers of the tamper-detection sensor embedded within the multilayer circuit board. Advantageously, the thickness and overall size of the vent structure disclosed herein allows insertion of the structure into the circuit board, and adequate adhesion between layers of the multilayer circuit board. In one or more implementations, the vent structure may include one or more vent channels (for instance, air passages) that are irregularly shaped, and may include one or more false paths, making a breach through the vent structure even more difficult.

In one or more embodiments, the tamper-detection sensor embedded within the multilayer circuit board includes multiple tamper-detect network layers, and the vent structure extends into the secure volume between a first tamper-detect network layer of the multiple tamper-detect network layers, and a second tamper-detect network layer of the multiple tamper-detect network layers.

In one or more implementations, the vent structure extends within the multilayer circuit board between the secure volume of the tamper-respondent assembly and an unsecure region external to the secure volume of the tamper-respondent assembly. Advantageously, the vent structure, with the one or more vent channels, couples in fluid communication the secure volume, or more particularly, a space within the secure volume, and the unsecured region external to the secure volume to, for instance, facilitate equalizing air pressure within the secure volume with air pressure external to the tamper-respondent assembly.

By way of example, FIGS. 7A & 7B depict one embodiment of a tamper-respondent assembly 300', in accordance with one or more aspects of the present invention. In one or more implementations, tamper-respondent assembly 300' may be similar to tamper-respondent assembly 300 described above in connection with FIGS. 3A-6, with an exception that one or more vent structures 710 are provided within multilayer circuit board 310 of tamper-respondent assembly 300'. Note in this regard that tamper-respondent assembly 300' may further include an enclosure (not shown) similar to enclosure 320 described above in connection with the embodiment of FIGS. 3A & 3B. The size, shape and configuration of the enclosure may be selected to facilitate defining the desired secure volume 301 between the enclosure and multilayer circuit board 310 of tamper-respondent assembly 300'. As in the embodiments described above, one or more tamper-detection sensors, such as one or more flexible tamper-detection sensors, are provided on the inner surfaces of the enclosure to facilitate defining secure volume 301 between the enclosure and an embedded tamper-detection sensor 700 within multilayer circuit board 310. In one or more implementations, embedded tamper-detection sensor 700 may include multiple tamper-detection layers, such as the above-described tamper-detection mat layers 400 and tamper-detection frames 401, discussed in connection with FIG. 4. As understood by one skilled in the art, the number, placement, and configuration of the tamper-detection mat layers and tamper-detection frames, or more generally, the embedded tamper-detection sensor 700, may be configured for the desired application.

As illustrated in FIG. 7B, embedded tamper-detection sensor 700 may include multiple tamper-detect network layers of conductive lines or traces, provided in any desired pattern to facilitate protection of secure volume 301, which in this example, is defined both above an upper surface of multilayer circuit board 310, and, partially, within multilayer circuit board 310.

As illustrated, vent structure 710 is incorporated or integrated (for instance, laminated) into multilayer circuit board 310, and includes one or more vent channels 711, which facilitate ventilation of a space within the secure volume 301. In this example, the space within secure volume 301 includes the space between the upper surface of multilayer circuit board 310 and the enclosure (not shown) with the tamper-detection sensor(s) on the inner surfaces thereof. Additionally, the space would include, in this example, an embedded cavity 712 disposed within multilayer circuit board 310, and a vent opening 713, such as a drill hole extending from the upper surface of the multilayer circuit board 310 within the secure volume, down into the multilayer circuit board such that the space above the multilayer circuit board within secure volume 301 is in fluid communication with the vent channel(s) 711 within vent plate 710. Note that in one or more embodiments, vent structure 710 may include multiple vent channels, and the at least one vent opening may be multiple vent openings. The vent opening(s) 713 could be formed by, for instance, mechanically drilling or laser drilling into the multilayer circuit board 310 to provide the fluid communication to, for instance, embedded cavity 712, which as noted, is in fluid communication with vent channel(s) 711 of vent plate 710.

As illustrated in FIGS. 7A & 7B, in one or more embodiments, the vent channel(s) 711 within vent structure 710 may extend between opposing ends of the vent structure 710, with opposite main sides of the vent structure being substantially parallel. In the depicted embodiment, the vent structure 710 is positioned such that the vent channel(s) extends to an edge of the multilayer circuit board 310. Advantageously, embedded cavity 712 is an enlarged cavity which facilitates fluid communication between vent opening 713 into multilayer circuit board 310 and vent channel(s) 711 within vent structure 710. By way of example, in one or more implementations, embedded cavity 712 may have a width approximately equal to the width of vent structure 710, and have any desired length into multilayer circuit board 310.

In one or more implementations, vent structure 710 may reside, or be sandwiched between, different layers of the multilayer circuit board 310. For instance, vent structure 710 may be adhesively secured or laminated within multilayer circuit board 310 between a second and fifth layer of the board, with the third and fourth layers being modified to accommodate vent structure 710. Additionally, vent structure 710 may be electrically isolated between layers of the multilayer circuit board, or alternatively, selectively, electrically connected to one or more tamper-detect networks of the embedded tamper-detection sensor 700 within the multilayer circuit board. Note that in one or more embodiments, vent structure 710 may reside in the region of the tamper-detection frames embedded within the multilayer circuit board and facilitating defining secure volume 301. In implementation, vent structure 710 crosses an interface or boundary of secure volume 301 within the board to facilitate venting of the space within the secure volume 301, as described herein.

As noted, in one or more implementations, vent structure 710 may be formed of a rigid or semi-rigid material, such as a thin metal, plastic, or polymer, and may include one or more vent channels 711 formed within specified tolerances to provide a "repeatable" flow rate or exchange rate between the space within secure volume 301 of the tamper-respondent assembly 300' and, for instance, an unsecure region external to the secure volume, such as ambient air about the tamper-respondent assembly. In one or more implementations, vent structure 700 is formed of a material selected to be transparent to, for instance, x-ray analysis of the tamper-respondent assembly. For instance, vent structure 710 could be fabricated of silicon or polyoxybenzylmethylenglycolanhydride, if desired. Also, vent structure 710 may be formed from a variety of fabrication techniques. For instance, vent structure 710 could be fabricated as a single part, such as by pad print, stereolithography (SLA), or other 3-D printing approach, or other methods, to create, for instance, a thin-vent plate with one or more irregular-shaped vent channels extending through the plate from, for instance, one end to the other.

Note that vent channel(s) 711 through vent structure 710 could be two-dimensional, or event three-dimensional, depending, for instance, on thickness of the vent structure. Two-dimensional in this context refers to the vent channel extending within, for instance, a common plane between the opposite ends of the vent plate, while three-dimensional would allow for the vent channel(s) to pass through the vent plate via multiple planes or layers of the vent plate. Note that vent structure 710 of FIGS. 7A & 7B is assumed to be a flat structure with, in one or more implementations, parallel opposing main surfaces. In one specific implementation, vent structure 710 is a rigid or semi-rigid structure, such as a metal structure, for instance, an aluminum, copper, or a stainless steel vent structure, with pieces soldered, welded, or braised together. In one implementation, the vent structure may be 1-10 mm wide by 0.2-0.3 mm in height, with a length selected as desired to extend from an edge of the circuit board through the secure volume interface defined by embedded tamper-detection sensor 700 into the secure volume 301 of multilayer circuit board 300'.

As noted, vent channel(s) 711 within vent structure 710 may include multiple directional changes of, for instance, 90°, or greater, such as in one or more zigzag patterns. Advantageously, providing embedded cavity 712 within multilayer circuit board 310 facilitates fluid communication coupling of one or more vent openings 713 into the circuit board with vent channel(s) 711 of vent structure 710. For instance, vent opening(s) 713 may be mechanically drilled or laser drilled, and the presence of embedded cavity 712 allows a certain amount of imprecision in the drilling process. This assumes that embedded cavity 712 has a larger footprint in plan view than the diameter of vent opening(s) 713.

Figure 8A:
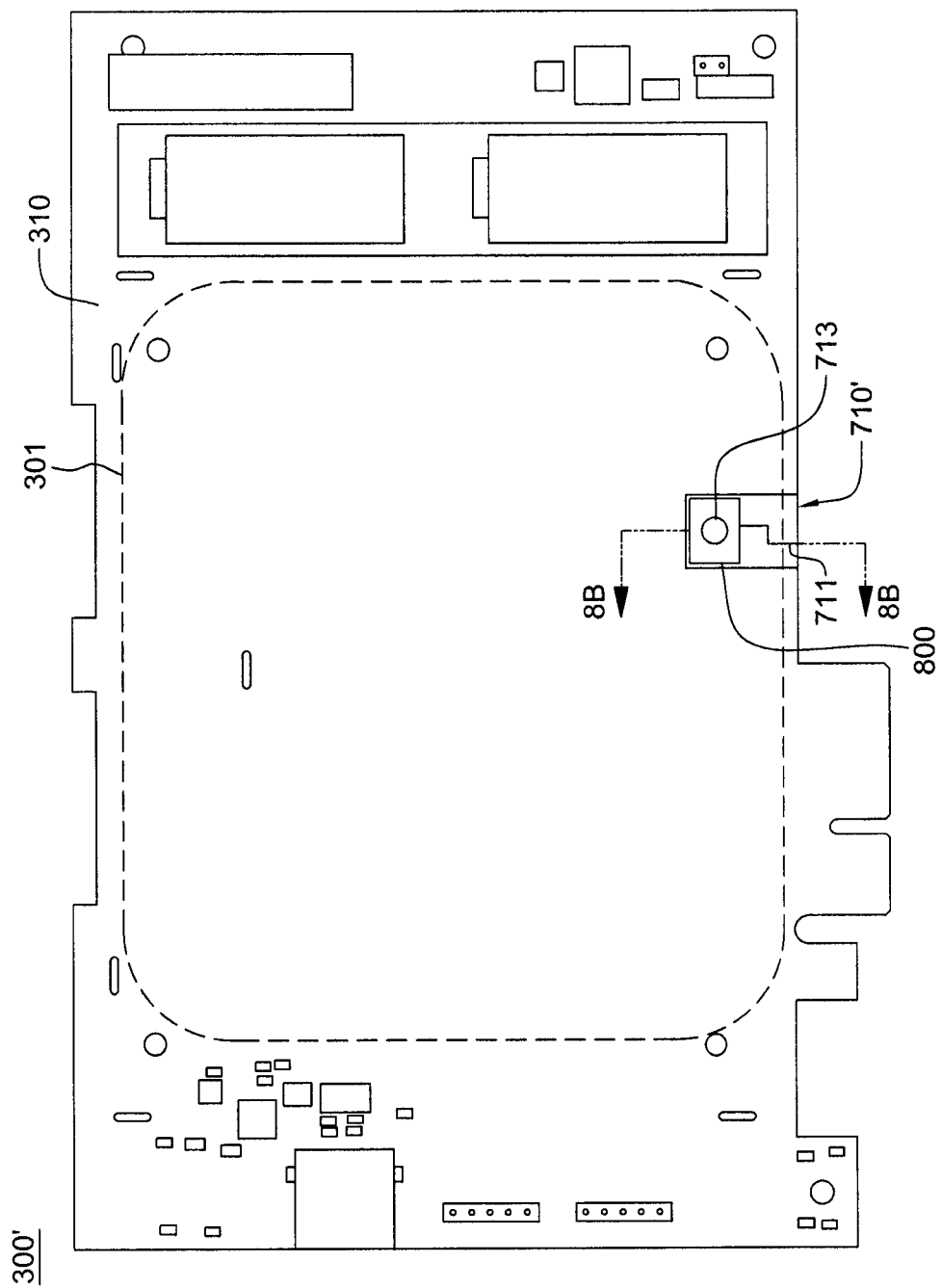
FIG. 8A is a plan view of another embodiment of a multilayer circuit board of a tamper-respondent assembly with an incorporated vent structure, in accordance with one or more aspects of the present invention.
Figure 8B:
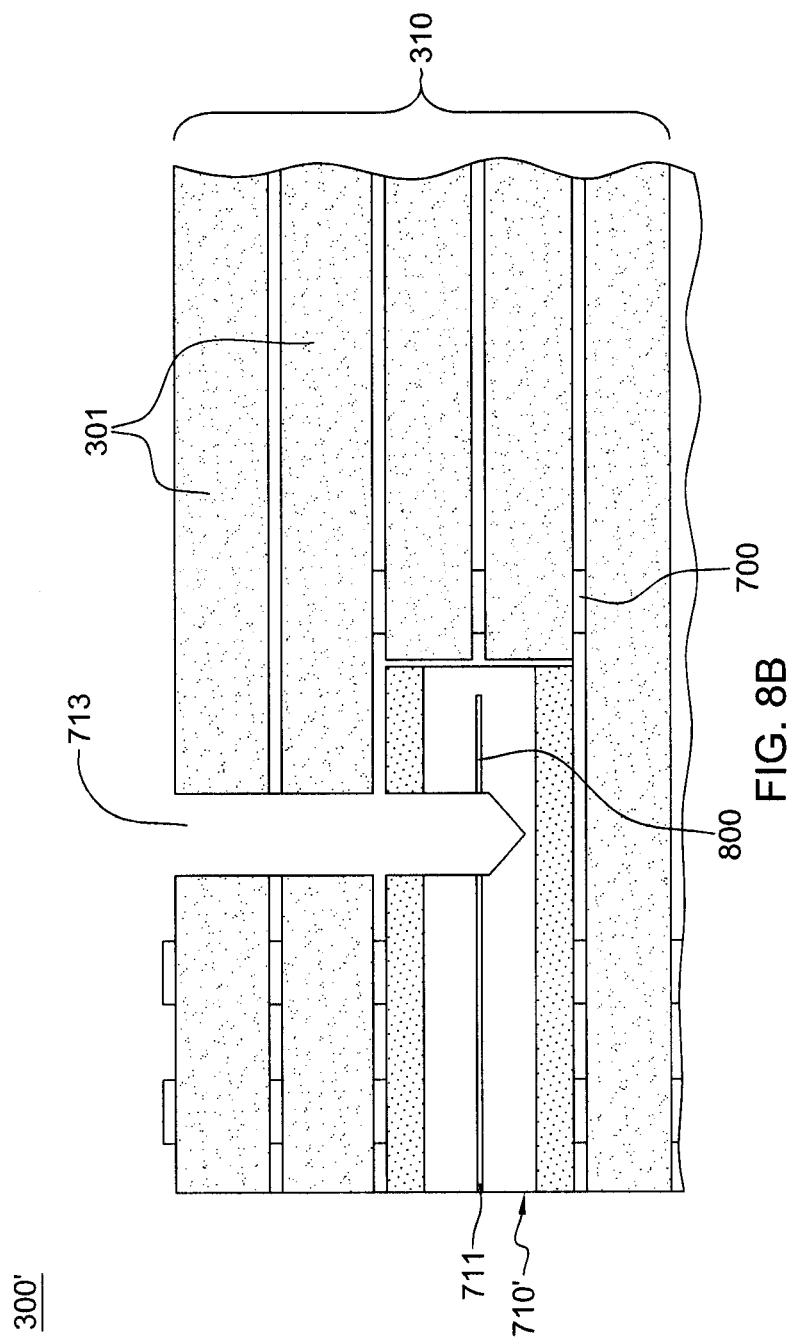
FIG. 8B is a cross-sectional elevational view of the multilayer circuit board and vent structure of FIG. 8A, taken along line 8B-8B thereof, in accordance with one or more aspects of the present invention.

FIGS. 8A & 8B depict an alternate embodiment of a tamper-respondent assembly 300', in accordance with one or more aspects of the present invention. In this embodiment, an alternate vent structure 710' is depicted. Vent structure 710' may be similar to vent structure 710 described above in connection with the embodiment of FIGS. 7A & 7B, with the exception that a vent cavity 800 is added within vent structure 170' in fluid communication with the one or more vent channels 711.

One embodiment of vent cavity 800 within vent structure 710' is depicted in plan view in FIG. 8A, and in elevational view in FIG. 8B. As illustrated, vent cavity 800 may be an enlarged cavity region of vent structure 710' which is larger than vent opening(s) 713 into multilayer circuit board 310, and which allows for a certain amount of imprecision in, for instance, mechanically drilling (or laser drilling) vent opening(s) 713 into the multilayer circuit board. With vent structure 710' in place within multilayer circuit board 310, vent opening(s) 713 may be drilled, with the vent structure material(s) (for instance, vent plate material(s)) indicating where the drilling process is to stop, that is, once the drill extends into, or even through, vent cavity 800 of vent structure 710'. In this configuration, the presence of vent cavity 800 within vent structure 710' eliminates the need for embedded cavity 712 within multilayer circuit board 310 provided in the embodiment of FIGS. 7A & 7B.

In one or more implementations, with incorporating vent cavity 800 into vent structure 710', the length of the vent structure is increased to allow sufficient area to provide the desired enlarged vent cavity 800 within the structure. Note that in one or more alternate embodiments, the shape and size of vent cavity 800 within vent structure 710' may vary, as desired for a particular application. For instance, the configuration and size of vent structure 710', including vent cavity 800, may be modified if multiple vent openings (e.g., drill holes) are to be made into multilayer circuit board 310 to be in fluid communication with the one or more vent channels 711 of vent structure 710'.

Figure 9B:
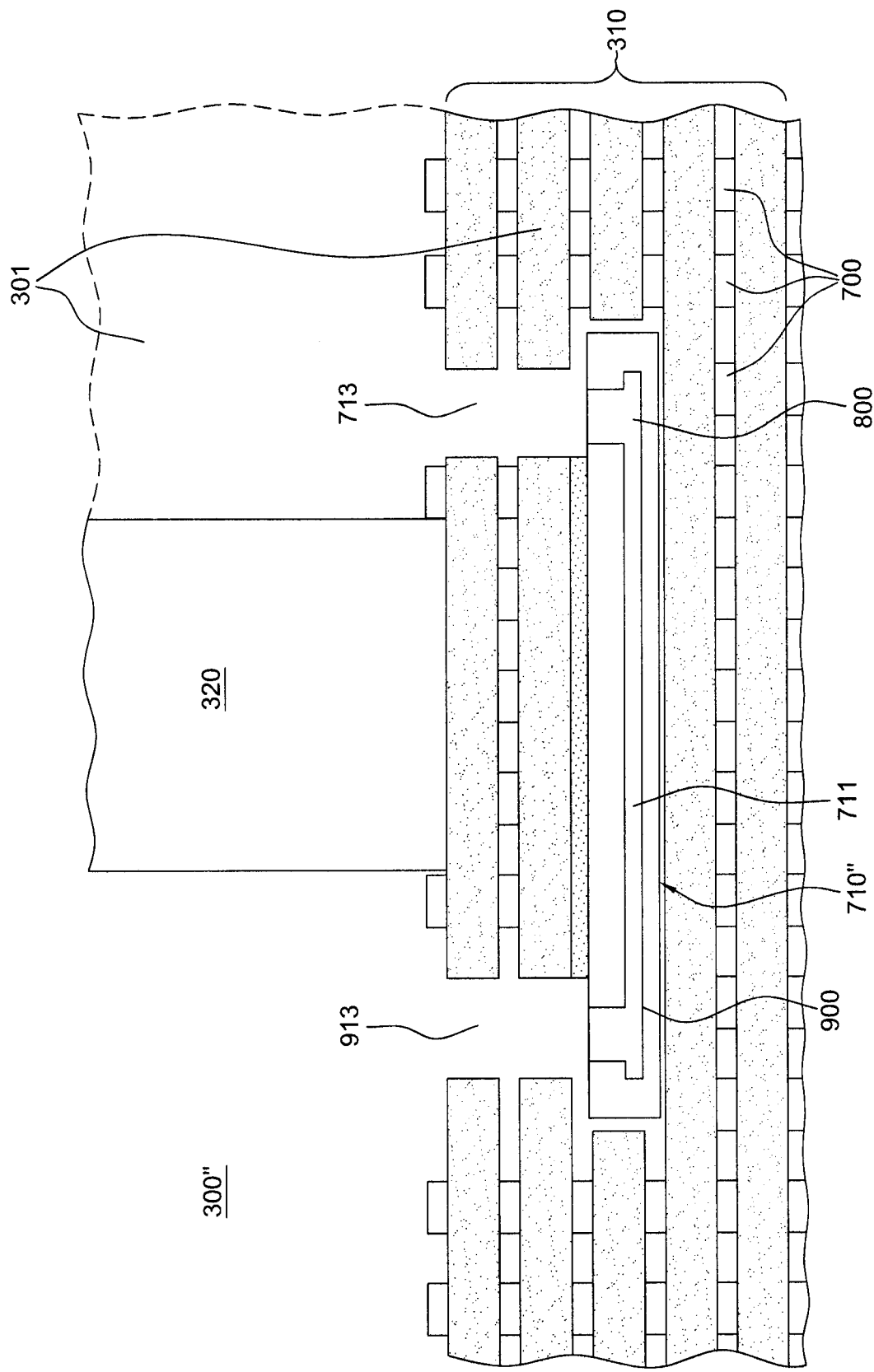
FIG. 9B is a cross-sectional elevational view of the multilayer circuit board and vent structure of FIG. 9A, taken along line 9B-9B thereof, in accordance with one or more aspects of the present invention.

FIGS. 9A & 9B depict an alternative tamper-respondent assembly 300", in accordance with one or more aspects of the present invention. In one or more implementations, tamper-respondent assembly 300" may be similar to tamper-respondent assembly 300 described above in connection with FIGS. 3A-6, as well as tamper-respondent assembly 300' described above in connection with FIGS. 7A-8B. However, in this implementation, a vent structure 710" is moved from an edge of multilayer circuit board 310 into the multilayer circuit board. As illustrated in FIG. 9A, vent structure 710" is sized, configured and positioned to cross the interface or boundary of secure volume 301 to facilitate venting of a space within secure volume 301, as described herein.

In one or more embodiments, vent structure 710" may be configured similarly to vent structure 710' described in relation to FIGS. 8A & 8B, with the exception of an additional vent cavity 900 external to secure volume 301 in fluid communication with vent channel(s) 711. This additional vent cavity 900 facilitates coupling in fluid communication one or more vent openings 913 outside secure volume 301 with one or more vent channels 711 within vent structure 710", and thus, coupling in fluid communication the space(s) within secure volume 301 with the unsecured region or space outside the secure volume, such as ambient air. Note that in an alternate embodiment, an embedded cavity (not shown) could be provided at one end or both ends of the vent structure, similar to embedded cavity 712 described above in connection with FIGS. 7A & 7B. In such implementations, the length of vent structure 710" may be shortened, and the respective vent cavities 800, 900 may be omitted with the vent openings 713, 913 being in fluid communication with the respective embedded cavity on the respective end of the vent structure.

Figure 10A:
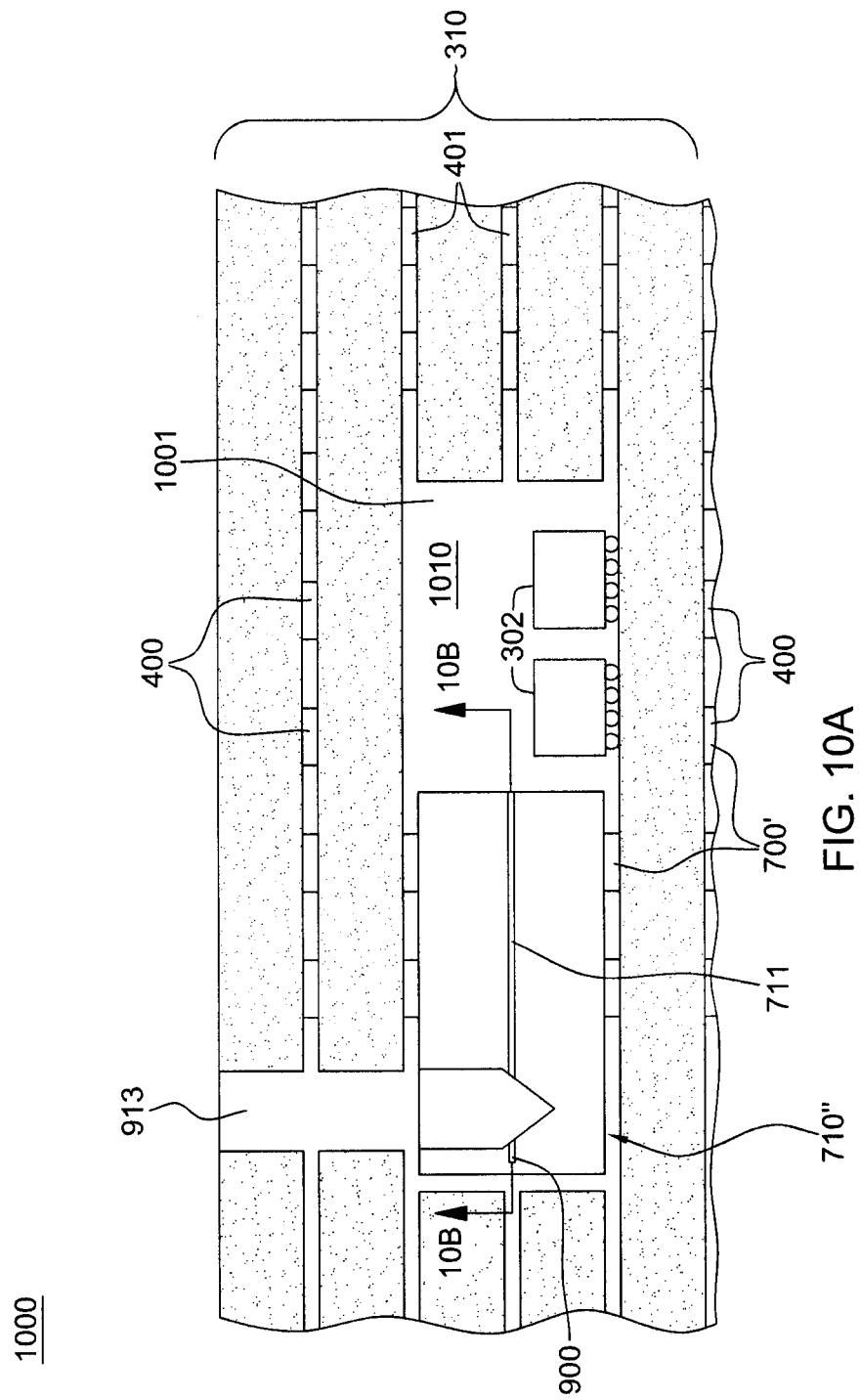
FIG. 10A is a cross-sectional elevational view of a further embodiment of a tamper-respondent assembly, including a multilayer circuit board and a vent structure incorporated into the multilayer circuit board, in accordance with one or more aspects of the present invention.
Figure 10B:
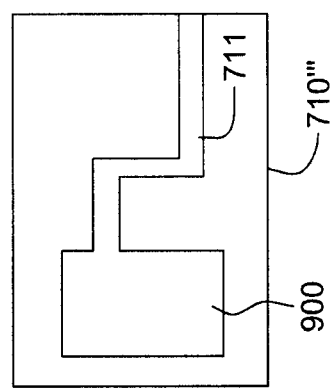
FIG. 10B is a plan view of one embodiment of the vent structure of FIG. 10A, in accordance with one or more aspects of the present invention.

FIGS. 10A & 10B depict a further variation on a tamper-respondent assembly, generally denoted 1000, in accordance with one or more aspects of the present invention. In this embodiment, a tamper-respondent assembly 1000 includes a multilayer circuit board 310 with an embedded tamper-detection sensor(s) 700' that defines a secure volume 1001 entirely within multilayer circuit board 310. In the depicted implementation, an embedded cavity 1010 is provided within secure volume 1001 which accommodates one or more electronic components 302 fully within multilayer circuit board 310. The embedded tamper-detection sensor 700 may be formed from an appropriate arrangement of tamper-detection mat layers 400 above and below embedded cavity 1010, and tamper-detection frames 401 along the sides of embedded cavity 1010. Further details of tamper-detection mat layers 400 and tamper-detection frames are described above in connection with FIG. 4. The size and configuration of secure volume 1001, as well as space 1010 within multilayer circuit board 310, may be selected as desired to accommodate, for instance, the number and size of electronic components 302 to be protected.

As depicted in FIGS. 10A & 10B, a vent structure 710''' may be provided similar to vent structure 710'' described above in connection with FIGS. 9A & 9B, with the exception that vent cavity 800 in the embodiment of FIGS. 9A & 9B is omitted in vent structure 700''', and vent channel(s) 711 are in direct fluid communication with embedded cavity 1010. In particular, as illustrated in FIG. 10B, one or more vent channels 711 may extend directly to an end of vent structure 710''', which would be open to and in fluid communication with embedded cavity 1010 within secure volume 1001 of multilayer circuit board 310. As noted above, the number, size, and configuration of vent channel(s) 711, as well as vent cavity 900, may vary depending upon the implementation desired.

As in the embodiments described above, vent opening(s) 913 is external to secure volume 1001, and together with vent structure 710''' allows for venting of embedded cavity 1010 within the multilayer circuit board. Further, as explained above, vent opening(s) 913 extends down into vent structure 710''' to intersect, and potentially extend past, vent cavity 900 within the vent structure to ensure good fluid communication between the one or more vent channels 711 of the vent structure 700''' and vent opening(s) 913. Thus, good fluid communication is established between the embedded cavity 1010, or space, within secure volume 1001 and an unsecure region, such as the ambient environment about tamper-respondent assembly 1000. If desired, more than one vent structure 710''' may be provided within tamper-respondent assembly 1000, each extending across the interface or boundary of secure volume 1001 to allow for venting of the embedded cavity 1010, or space, within the secure volume containing the electronic component(s) to be protected.

Figure 11:
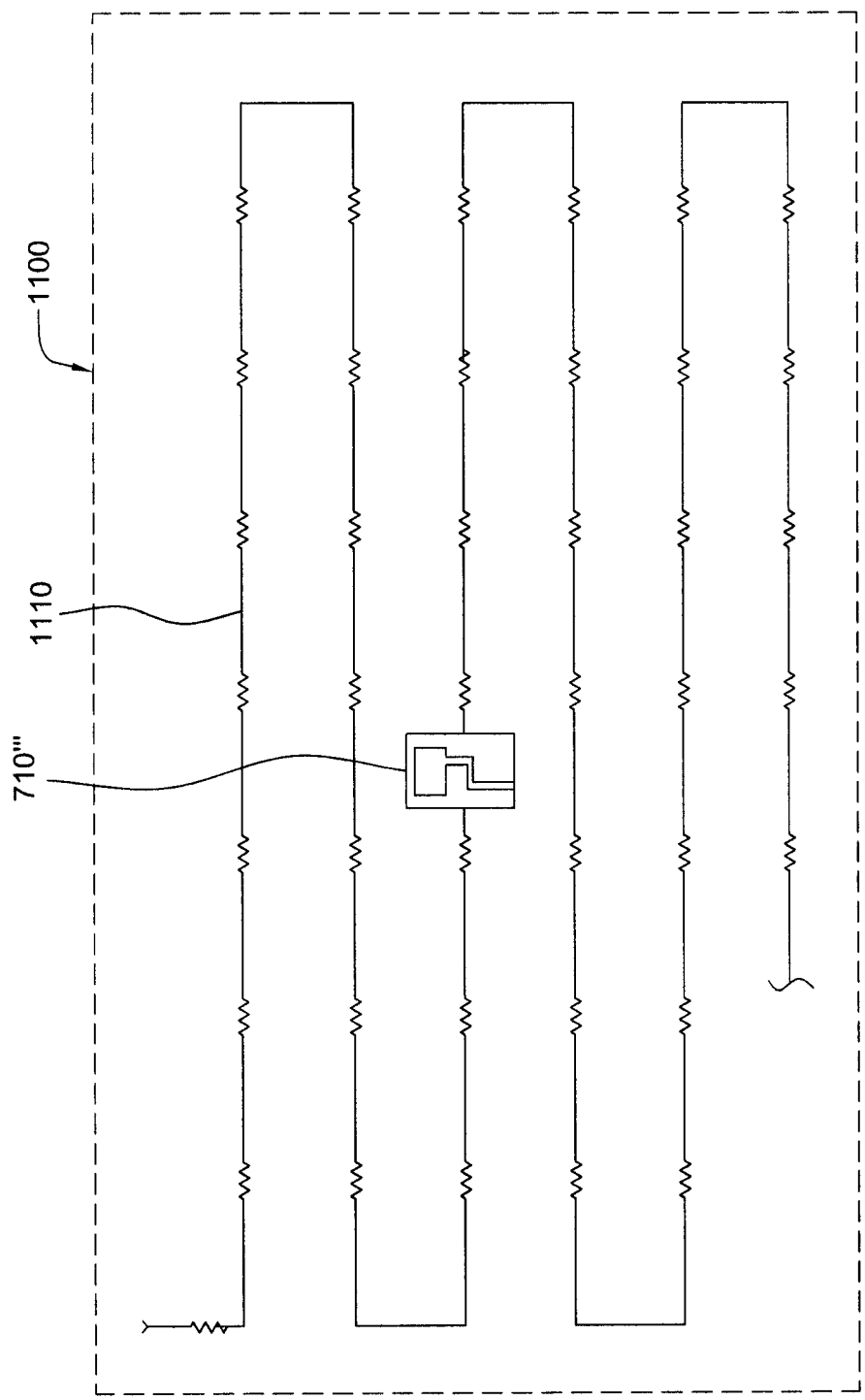
FIG. 11 is a partial schematic of one embodiment of a tamper-detect network layer of a tamper-detection sensor embedded within a multilayer circuit board of a tamper-respondent assembly, and electrically incorporating a vent structure within the tamper-detect network, in accordance with one or more aspects of the present invention.

FIG. 11 illustrates a further enhancement which may be used within a vented tamper-respondent assembly such as described herein, for instance, in relation to the assemblies of FIGS. 7A-10B. In particular, in one or more implementations, the vent structure, such as vent structure 710''' of FIGS. 10A-10B, may be fabricated of an electrically conductive material, and the vent structure may be electrically connected in one (or possibly more) tamper-detect network(s) 1110 of the embedded tamper-detection sensor 700' (FIG. 10A) within the multilayer circuit board. In such a configuration, rather than being electrically isolated from circuitry within the multilayer circuit board, the vent structure 700''' is electrically connected to, for instance, one of the tamper-detect networks 1110, such as to one or more of the tamper-detection frames 401 in the example of FIGS. 10A & 10B. Note in this regard that tamper-detect network 1110 of FIG. 11 within a tamper-detect network layer 1100 may be formed of any desired configuration, as well as any desired line size and line spacing, as described above in connection with FIGS. 2-5. In the example of FIG. 11, resistive monitoring of the tamper-detect network 1110 may be employed to monitor for a tamper event. For instance, should a tamper event be attempted through vent structure 710''', then a resistance change will likely occur within the tamper-detect network 1110, which allows for the tamper event to be identified and, for instance, action taken to protect the confidential information within the secure volume of the tamper-respondent assembly.

By way of further enhancement, disclosed herein are additional vented tamper-respondent assemblies and methods of fabrication which incorporate an in situ vent structure. As used herein, "in situ vent structure" refers to a vent structure formed in place, or in situ, within, for instance, a multilayer circuit board, such as described herein. Aside from being formed in place, for instance, within a circuit layer of the multilayer circuit board, the in situ vent structures described hereinbelow may be similar in structure, function and placement to those described above in connection with FIGS. 7A-11 (i.e., unless otherwise indicated).

Advantageously, the one or more in situ vent structures may each include one or more vent channels to facilitate, for instance, air ventilation of a secure volume, or more particularly, a space within the secure volume, of the tamper-respondent assembly. The in situ vent structure(s) may be fabricated using the same processes as used to, for instance, fabricate by building up the multilayer circuit board. The in situ vent structure(s) is advantageously difficult to detect, being fabricated, for instance, within an electrical circuit layer of the multilayer circuit board from multiple circuit line structures. For instance, the vent structures would be difficult to discriminate from other electrical circuits using x-ray analysis. If desired, redundant in situ vent structures may be provided, and the vent structures may be disposed anywhere within the multilayer circuit board so as to cross the boundary or interface of the secure volume defined within or in association with the multilayer circuit board.

In one or more implementations, the vent openings may be hidden in the unsecure region of the tamper-respondent assembly by, for instance, placing the hidden vent opening under another mounted component. Further, vent openings may be constructed to look substantially identical to normal vias, and may include, for instance, a false round land around the hole to mirror round lands of via connects into the multilayer circuit board.

In one or more embodiments, respective vertical z-controlled drill openings provide the vent opening in fluid communication with the vent channel(s) of the in situ vent structure(s), both within the secure volume, and within the unsecure region. The vent channels may have any desired length, and the in situ vent structure(s) may have any desired size or configuration so as to be intermixed with, for instance, circuit lines of an electrical circuit layer of the multilayer circuit board.

FIGS. 12A-15 depict various additional embodiments of a tamper-respondent assembly incorporating one or more in situ vent structures, in accordance with one or more aspects of the present invention. As noted, unless otherwise indicated, the structure, configuration, placement, size, etc., of these in situ vent structures may be similar to the vent structures described above, with an exception being that the in situ vent structures are formed in place during fabrication of the multilayer circuit board using, for instance, the same or similar fabrication processes used in fabricating the multilayer circuit board. For instance, the in situ vent structure(s) may be formed contemporaneous with forming one or more electrical circuit layers of the multilayer circuit board, for instance, using the same conductive material as used in forming the circuit lines. In particular, multiple circuit line structures may be formed in a desired area of the multilayer circuit board to define, at least in part, the in situ vent structure(s).

Thus, disclosed herein, in general, are tamper-respondent assemblies which include a multilayer circuit board; a tamper-detection sensor embedded within the multilayer circuit board, the tamper-detection sensor defining, at least in part, a secure volume associated with the multilayer circuit board; and at least one in situ vent structure within the multilayer circuit board. The at least one in situ vent structure includes at least one vent channel, with the at least one vent channel being in fluid communication with a space within the secure volume to facilitate venting the space within the secure volume.

In one or more implementations, the in situ vent structure(s) includes multiple circuit line structures with a cover foil disposed over, at least in part, the multiple circuit line structures. The multiple circuit line structures are sized and configured to facilitate defining the in situ vent structure, with the at least one vent channel residing underneath the cover foil. By way of example, the cover foil may be a thin metal plate or foil placed on top of the multiple circuit line structures, which together define the vent channel(s) and, in one or more embodiments, embedded vent cavities at the ends of the vent channels. The cover foil may be formed, for instance, of the same material as used to form the multiple circuit line structures. Once placed over the multiple circuit line structures (for instance, to cover at least a desired section), subsequent lamination steps in the multilayer circuit board fabrication cycle lock the foil in position, tenting the circuit line structures, and defining the vent channels of the in situ vent structure(s).

In one or more embodiments, the in situ vent structure(s) may reside within an electrical circuit layer of the multilayer circuit board, such as within a tamper-detect network layer of the embedded tamper-detection sensor. In these embodiments, circuit lines of the electrical circuit layer may be formed of a conductive material, and the multiple circuit line structures of the in situ vent structure(s) may also be formed of the same conductive material. For instance, the circuit lines, circuit line structures, and cover foil may each be formed of copper, a copper alloy, or other metal or metal alloy, by way of example only.

In enhanced implementations, one or more of the circuit line structures of the multiple circuit line structures may be configured to define at least one probing trap within the at least one vent channel of the in situ vent structure(s). The probing trap may take any one of various configurations, and may include false corners to hinder an attempted tamper event through the in situ vent structure(s).

In one or more other embodiments, vent openings within the secure volume, as well as the unsecure region, may be concealed to look like normal vias with, for instance, a round LAN surrounding a vent opening on a surface of the multilayer circuit board. Additionally, in one or more embodiments, the vent opening in the unsecure region may be disposed underneath another structure, such as underneath a slightly raised electronic component or mechanical structure, such as, a battery holder of the tamper-respondent assembly. Additionally, in one or more implementations, multiple in situ vent structures may be provided, either within the same layer of the multilayer circuit board, or different layers of the multilayer circuit board. For instance, two or more in situ vent structures may be located in different layers of the multilayer circuit board. Additionally, vent openings to the in situ vent structures may be from either main surface of the multilayer circuit board, or both main surfaces, as desired.

As noted, the in situ vent structures described herein may be similar to the vent structures described above, and may be implemented in a variety of configurations. For instance, the in situ vent structures may include vent channels with one or more directional changes of 90°, or greater, and may include one or more zigzag directional changes, if desired. The vent channels within the in situ vent structures may be extremely small, with characteristic dimensions of (for instance) 0.1-0.2 mm, such as 0.15 mm, or smaller. In one or more implementations, the in situ vent structure extends within the multilayer circuit board between the secure volume of the tamper-respondent assembly and the unsecured region, external to the secure volume.

Advantageously, the one or more in situ vent structures, with the one or more vent channels, couple in fluid communication the secure volume, or more particularly, a space within the secure volume, and the unsecured region external to the secure volume to, for instance, facilitate equalizing air pressure within the secure volume with air pressure external to the tamper-respondent assembly.

Figure 12A:
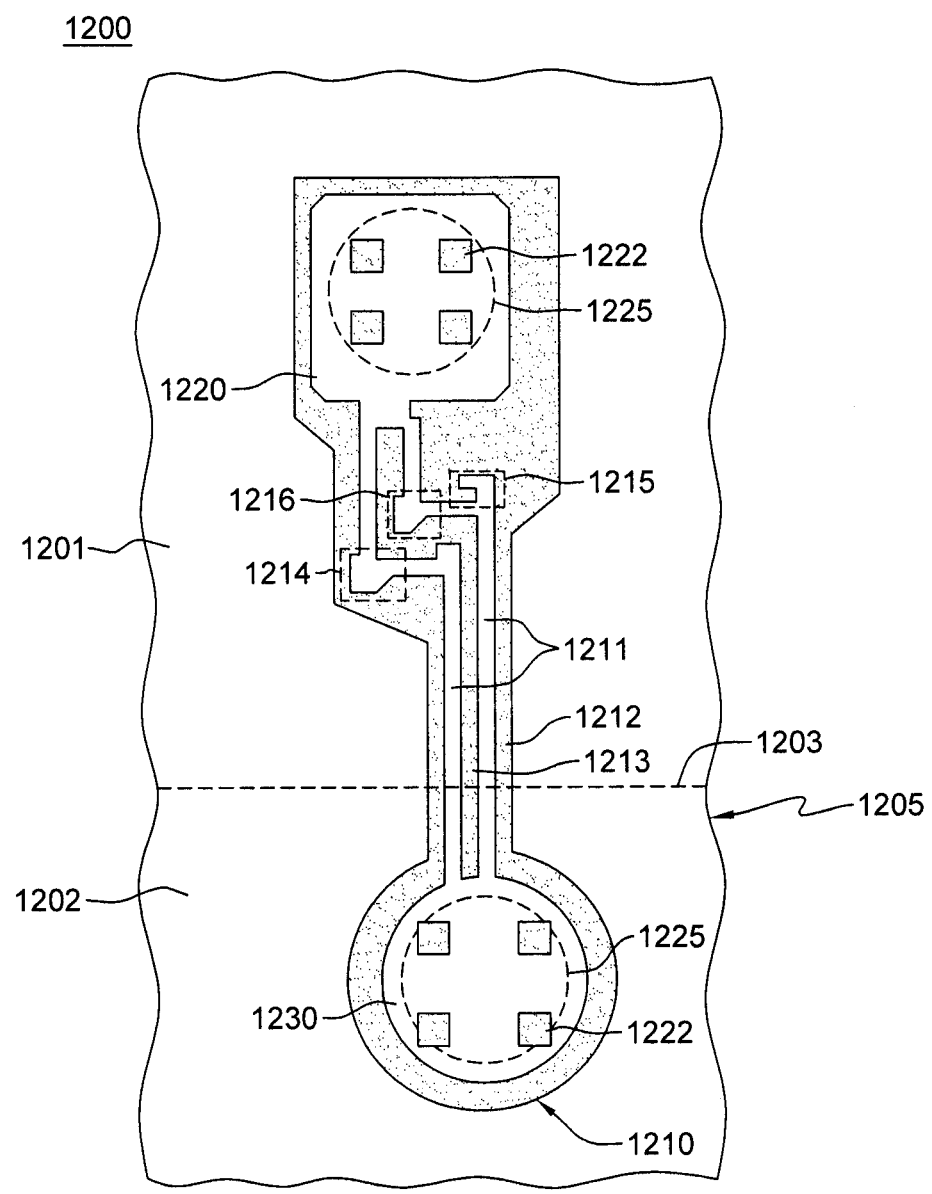
FIG. 12A is a cross-sectional plan view of one embodiment of an in situ vent structure within a multilayer circuit board of a tamper-respondent assembly, in accordance with one or more aspects of the present invention.
Figure 12B:
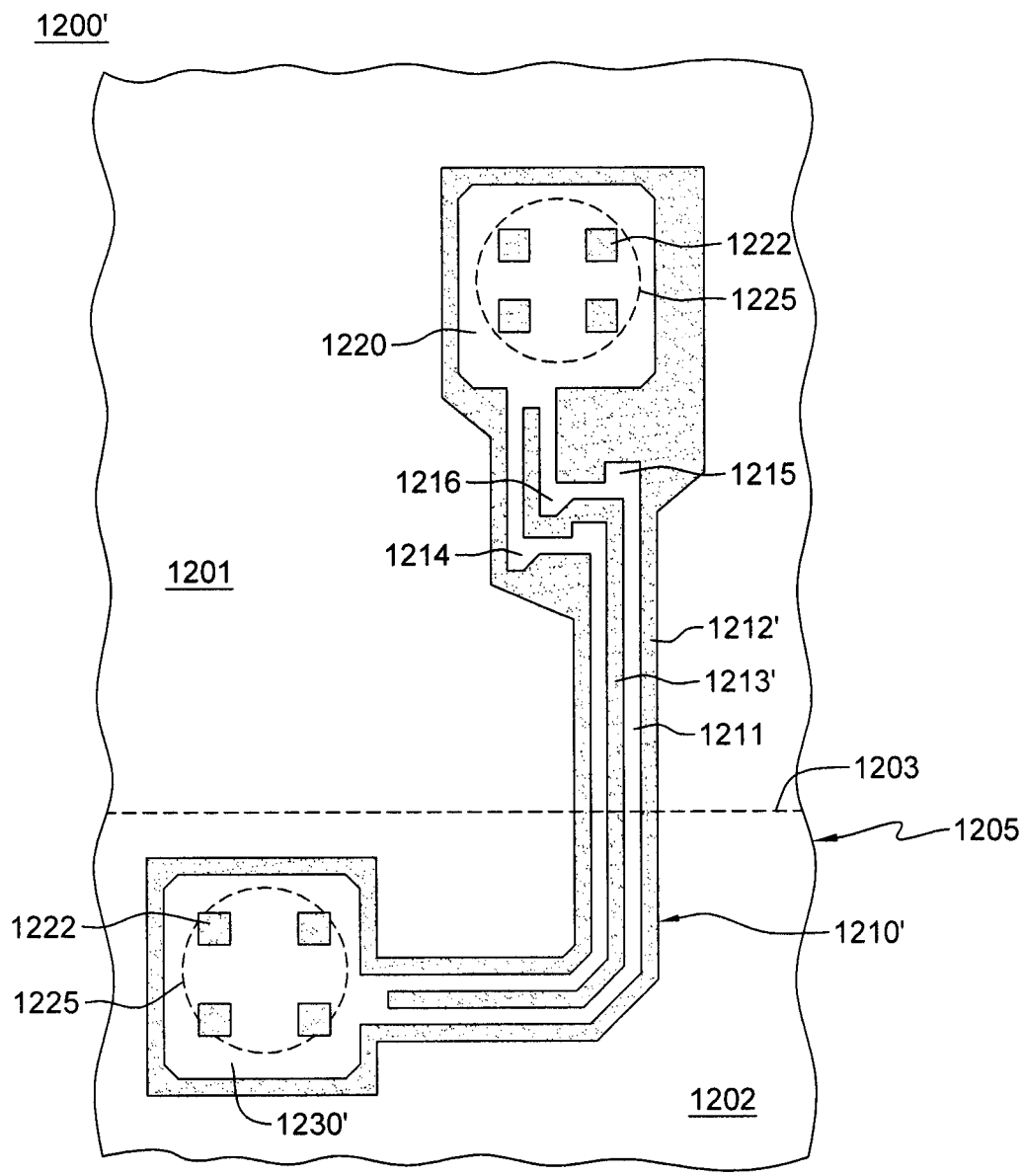
FIG. 12B is a cross-sectional plan view of a further embodiment of an in situ vent structure within a multilayer circuit board of a tamper-respondent assembly, in accordance with one or more aspects of the present invention.
Figure 12C:
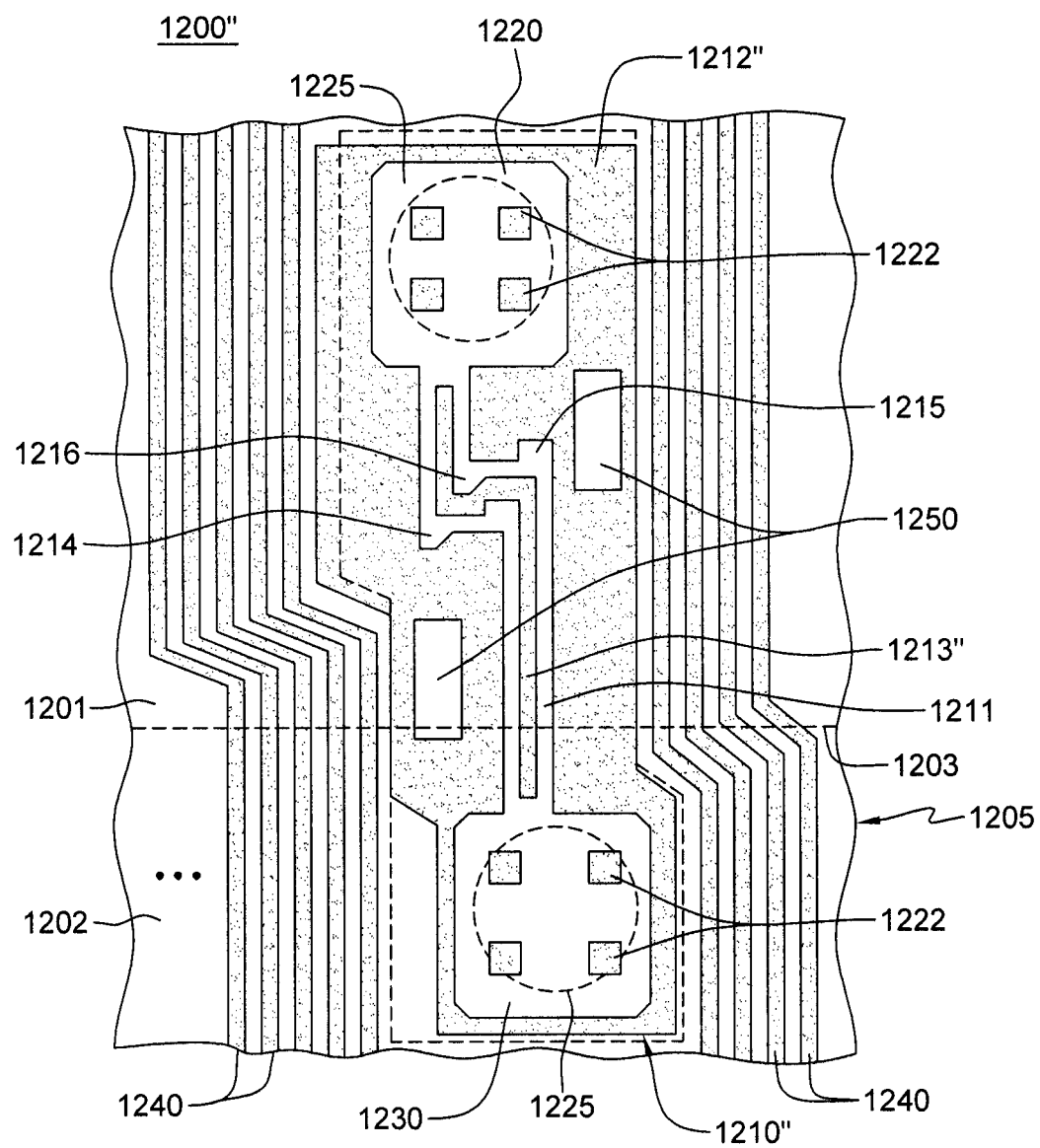
FIG. 12C is a cross-sectional plan view of another embodiment of an in situ vent structure within a multilayer circuit board of a tamper-respondent assembly, in accordance with one or more aspects of the present invention.

By way of example, FIGS. 12A-12C depict cross-sectional plan views of a tamper-respondent assembly 1200, 1200', 1200", respectively, which includes a secure volume 1201 and unsecure region 1202 within a multilayer circuit board 1205, such as described herein. In these figures, an in situ vent structure 1210, 1210', 1210", respectively, is illustrated, formed from multiple circuit line structures. For instance, in the example of FIG. 12A, an outer circuit line structure 1212 and an inner circuit line structure 1213 are provided to define vent channels 1211 in association with a cover foil (not shown) overlying, for instance, at least the middle region of circuit line structures 1212, 1213, including at the boundary 1203 of secure volume 1201.

FIGS. 12B & 12C depict similar in situ vent structures, with an outer circuit line structure 1212', 1212", and an inner circuit line structure 1213', 1213", defining vent channels 1211. In each embodiment, one or more of the circuit line structures may be configured to define one or more probing traps 1214, 1215, 1216 within vent channel 1211 to inhibit the ability of a probe to be inserted through vent channels 1211 as part of a tamper event. These probe traps 1214, 1215, 1216 may include one or more false corners, as desired, to prevent a tamper event through the vent channels.

As with certain vent structures described above, for instance, in relation to FIGS. 9A & 9B, in situ vent structures 1210, 1210', 1210" may each include a first vent cavity 1220 and a second vent cavity 1230 positioned, sized and configured, as desired for a particular application. The first and second vent cavities 1220, 1230 are in fluid communication with the vent channel(s) 1211, and facilitate coupling in fluid communication vent openings formed in the multilayer circuit board 1205 from, for instance, an upper surface of the multilayer circuit board within the secure volume 1201 and the unsecured region 1202, as described herein.

By way of specific example, the vent opening(s) (not shown) may be formed from a drill operation with a drill diameter 1225 depicted in FIGS. 12A-12C. In this configuration, support pads or pillars 1222 may be provided during the in situ vent structure fabrication process. These pads 1222 or pillars advantageously prevent collapse of the cover foil during the fabrication process, and may be contacted or removed during formation of the vent opening(s), in one or more implementations. Note that in alternate implementations, the support pads or pillars 1222 could remain in place, depending for instance, on their size and location within the respective vent cavity (not shown), as well as, for instance, the drill diameter 1225 used to form the vent opening in fluid communication with the vent cavities 1220, 1230. In one more implementations, support pads or pillars 1222 may be formed of the same material as used to form the multiple circuit line structures. Alternatively, other materials may be used, such as fully cured thermoset plastics, which are advantageously not visible to x-ray inspection.

As illustrated in FIG. 12C, one or more of the circuit line structures, such as outer circuit line structure 1212" may include nests or spaces 1250, if desired, to allow for an adhesive material to be employed on the underside of the cover foil (not shown) to overlie the circuit line structures 1212", 1213" of the in situ vent structure 1210", and facilitate anchoring the cover foil in place over the circuit line structures, in order to form the in situ vent structure, as described herein. Further, as illustrated in FIG. 12C, the in situ vent structure 1210" may be positioned within an electrical circuit layer of multilayer circuit board 1205 so as to be disposed between circuit lines 1240 of the electrical circuit layer. In one or more implementations, the electrical circuit layer within which the in situ vent structure(s) resides may be, for instance, a tamper-detect network layer of the embedded tamper-detection sensor, if desired. Alternatively, the electrical circuit layer could comprise signal wiring to electrically connect, for instance, one or more electronic components within the secure volume, to electrical components external the secure volume.

FIGS. 13A-13F illustrate one embodiment of a process for fabricating one or more in situ vent structures within a multilayer circuit board of a tamper-respondent assembly, in accordance with one or more aspects of the present invention. In this discussion, the tamper-respondent assembly may include, for instance, the multilayer circuit board, as well as an enclosure coupled to the multilayer circuit board, with the enclosure and board enclosing, at least in part, at least one electronic component to be protected. A tamper-detection sensor is embedded within the multilayer circuit board, and the tamper-detection sensor defines, at least in part, a secure volume associated with the multilayer circuit board. Additionally, as explained herein, within the multilayer circuit board, one or more in situ vent structures are formed in place. Each in situ vent structure includes one or more vent channels which are in fluid communication with a space within the secure volume to facilitate venting the space of the secure volume.

Figure 13A:
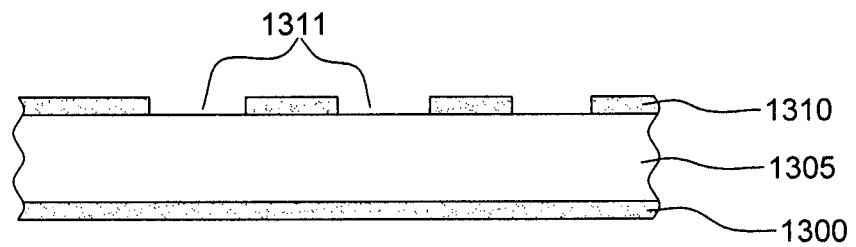
FIG. 13A-13F illustrate one embodiment of a process for fabricating one or more in situ vent structures within a multilayer circuit board of a tamper-respondent assembly, in accordance with one or more aspects of the present invention.

As illustrated in FIG. 13A, an intermediate stack during the multilayer fabrication process may include an electrical circuit layer 1300 formed of a patterned conductive material, as well as a dielectric layer 1305, and an additional electrical circuit layer 1310. In this case, additional electrical circuit layer 1310 is patterned with specially-configured openings 1311 where desired, between multiple circuit line structures of electrical circuit layer 1310. In one example, FIG. 13A is a partial, elevational cross-sectional view of the in situ vent structures of FIGS. 12A-12C, for instance, in the region of the secure volume boundary 1203, wherein the vent channels are in the process of being formed within the in situ vent structure(s). As one example, the thickness of dielectric layer 1305 may be approximately 100-150 μm, and the thickness of the electrical circuit layers 1300, 1310 may be approximately 30-40 μm, with patterned openings or channels 1311 having a width of approximately 50-100 μm (in one specific example only).

Figure 13B:
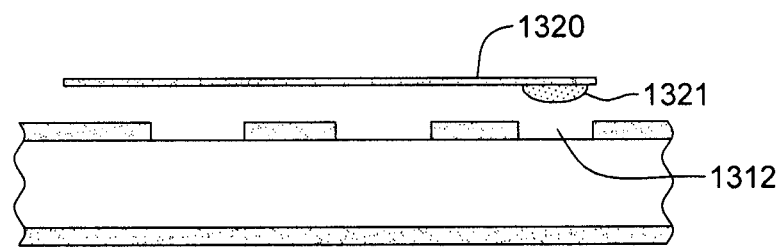

As illustrated in FIG. 13B, to create the vent channels, a thin cover foil 1320 is overlaid on top of the patterned circuit line structures defining openings 1311 in order to cover the openings and thereby form the vent channels 1311' (FIG. 13C) from the openings. Cover foil 1320 may be, for instance, a solid plate of metal having, for instance, a thickness of 10-25 μm, and a width and length based on the available room over the in situ vent structure(s) being fabricated. As noted, in one or more embodiments, the cover foil may be formed of the same material as used to form the circuit line structures. In one or more implementations, cover foil 1320 is overlaid onto the patterned circuit line structures of the in situ vent structure without an adhesive material between the cover foil and the circuit line structures. As noted, however, an adhesive (or other anchoring material) 1321 could be provided, along with an anchoring nest 1312 (such as anchoring nest 1250 described above in connection with FIG. 12C). Note that in implementation, the adhesive may be offset from the vent channels, and the cover foil creates the open channels for ventilation between, for instance, vent cavities formed at opposite ends of the vent channels, as depicted, by way of example, in FIGS. 12A-12C.

Figure 13C:
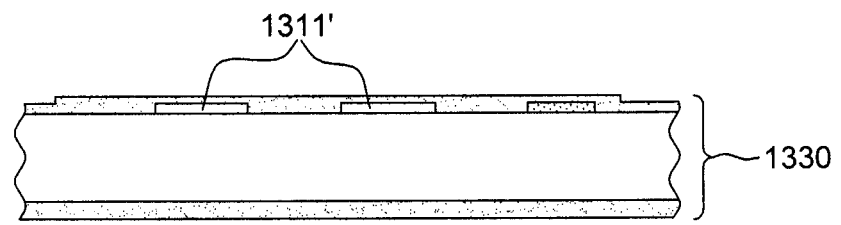
Figure 13D:
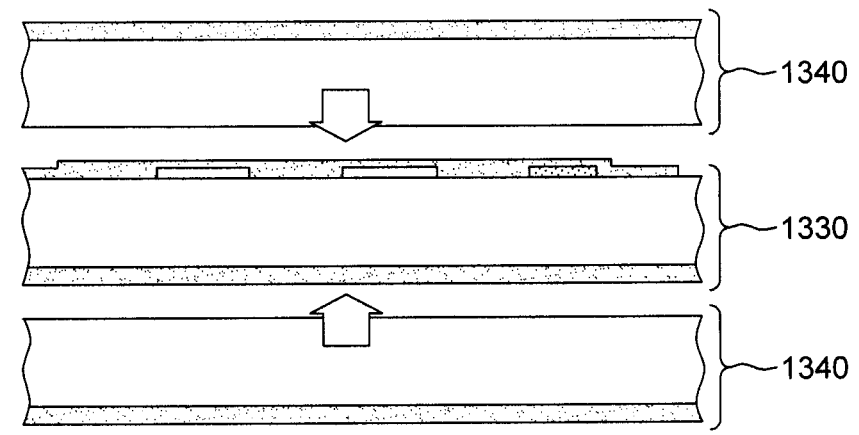

FIG. 13C illustrates one embodiment of the resultant structure, with the cover foil overlaid on top of the circuit line structures forming the in situ vent structure, including the vent channels. This intermediate structure 1330 may have other circuit layers 1340 laminated to both sides of the intermediate structure 1330, as illustrated in FIG. 13D, to create the structure 1350 of FIG. 13E. Note that, during this fabrication process, the in situ vent structure may be formed as a circuit feature, in the same steps as forming the electrical wiring layer within which the in situ vent structure is defined. The plating and etching of the conductive material to form the multiple circuit line structures may occur contemporaneously with the plating and etching of the circuit lines of the electrical circuit layer. As noted, as part of this process, vent cavities may also be defined within the in situ vent structure at opposite ends of the vent channels. As part of defining the vent cavities, one or more support pads or pillars may be formed within the vent cavities, as noted above in connection with FIGS. 12A-12C. The cover foil 1320 (FIG. 13B) may overlie the vent cavities as well to prevent the cavities from being clogged when the intermediate structure 1330 (FIG. 13D) is laminated with the additional electrical circuit layers 1340 overlying intermediate structure 1330 within the multilayer circuit board.

Figure 13E:
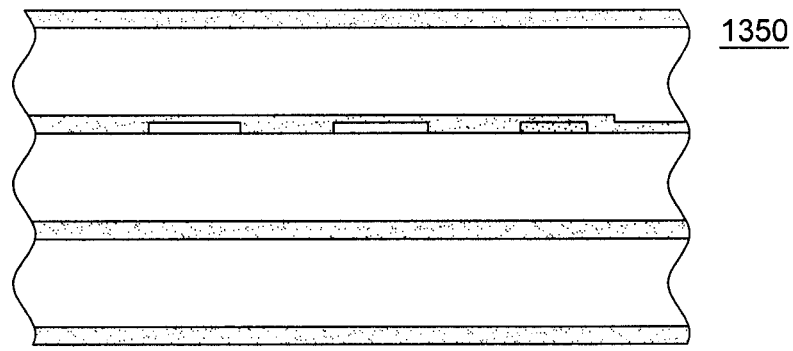
Figure 13F:
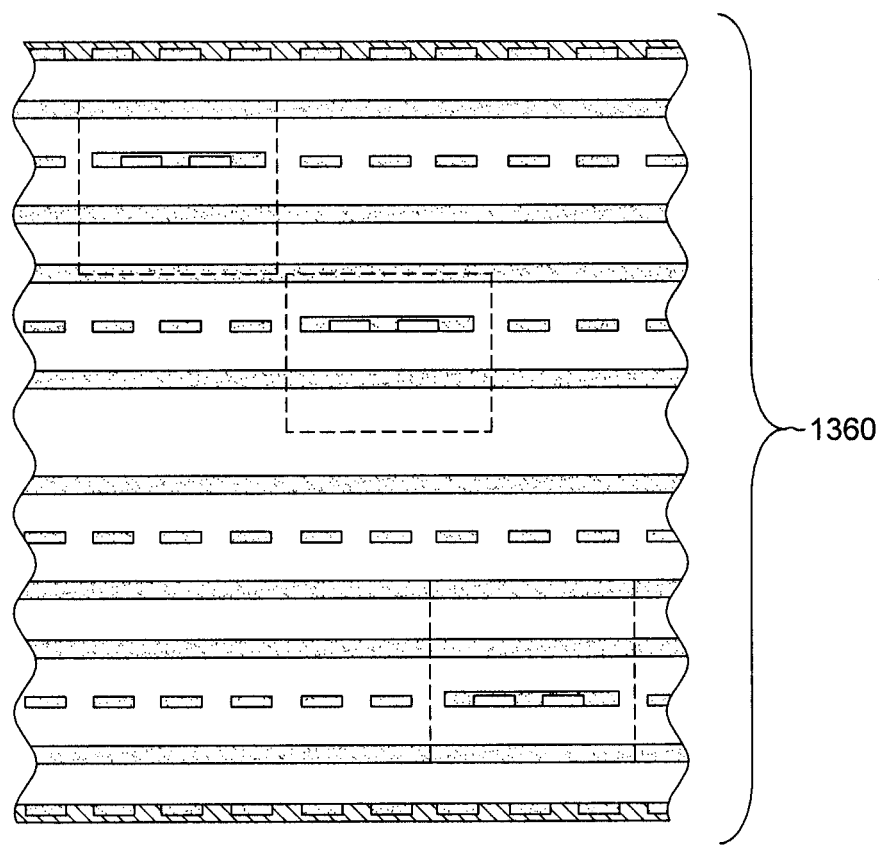

FIG. 13F depicts one embodiment of a multilayer circuit board 1360 comprising (for instance) the structure of FIG. 13E, as well as multiple in situ vent structures in different layers, such as in different electric circuit layers, of the multilayer circuit board.

Figure 14A:
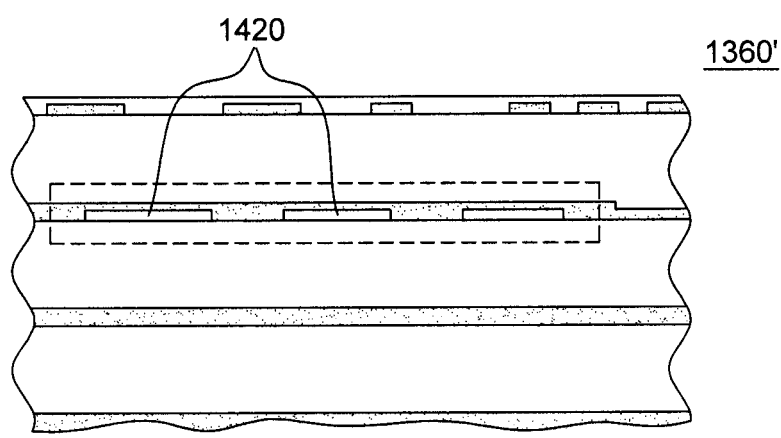
FIGS. 14A-14C illustrate one embodiment of a process for forming one or more vent openings in fluid communication with an in situ vent structure within a multilayer circuit board of a tamper-respondent assembly, in accordance with one or more aspects of the present invention.
Figure 14B:
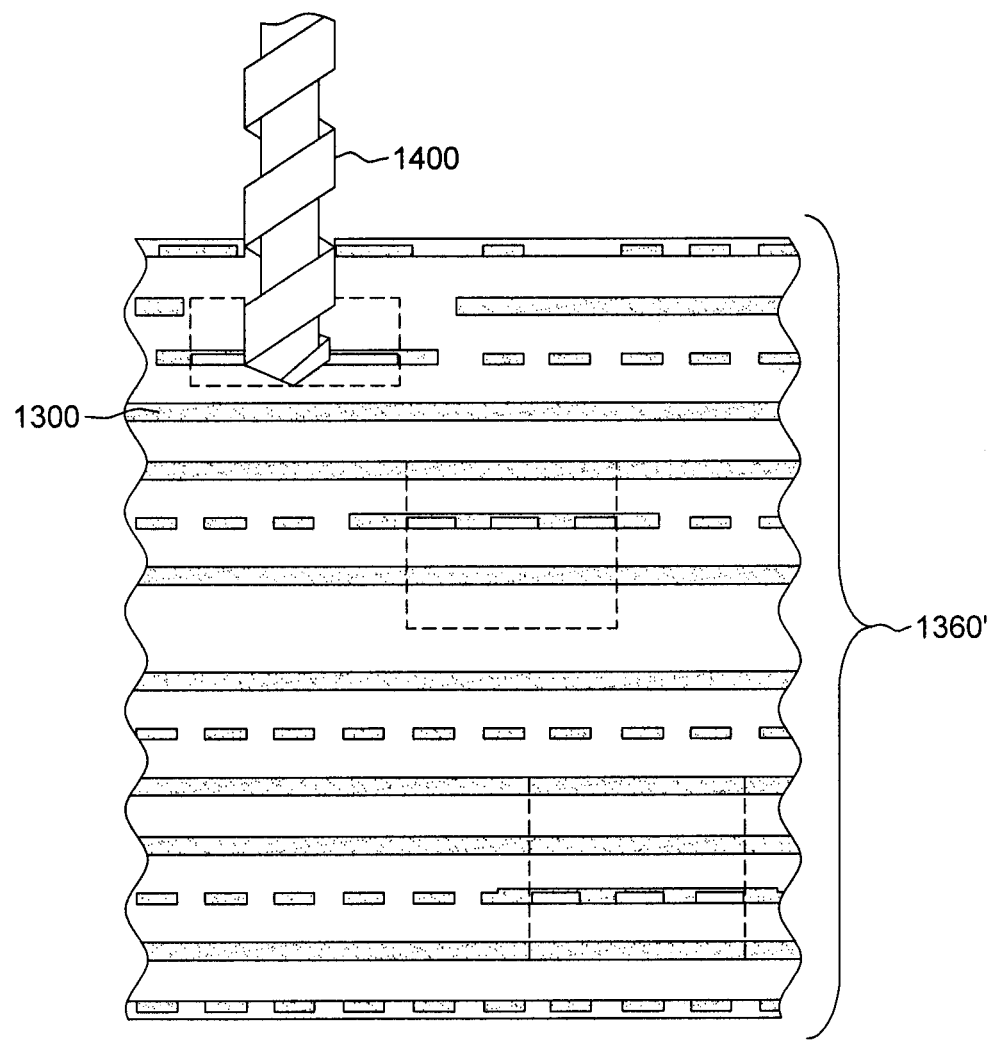
Figure 14C:
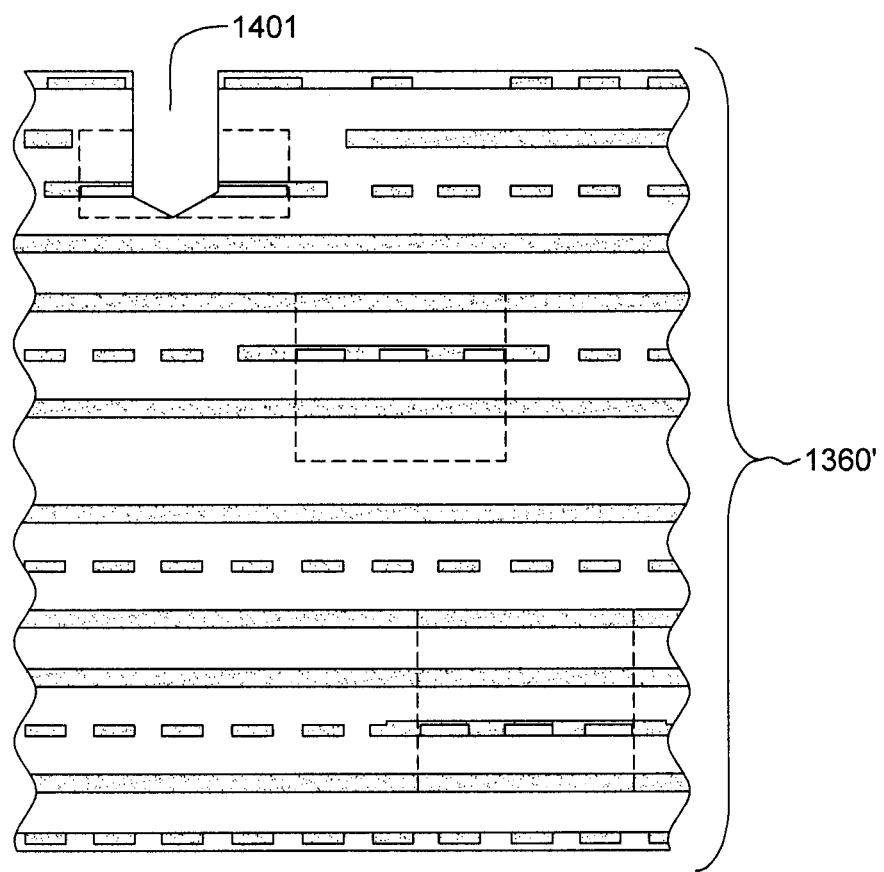

FIGS. 14A-14C depict one embodiment for z-controlled drilling vertically into a multilayer circuit board 1360'. As illustrated, in one or more implementations, a mechanical drill 1400 (FIG. 14B) may be employed to penetrate vertically multilayer circuit board 1360', such as in drilling a conductive via opening. The drill 1400 (whether mechanical or laser) may stop within the respective vent cavity 1420 of the in situ vent structure in communication with the vent channels of the vent structure, establishing a vent opening 1401, as illustrated in FIG. 14C. The thickness of the inner layers of the multilayer circuit board advantageously allow large tolerance in drilling depth. Further, the underneath metal layer 1300 (FIG. 14B) could be employed as a metal stop layer. As illustrated in these figures, the drill 1400 forming vent opening 1401 may, in one or more embodiments, remove one or more of the pads or supports within the respective vent cavity 1420 of the in situ vent structure.

Figure 15:
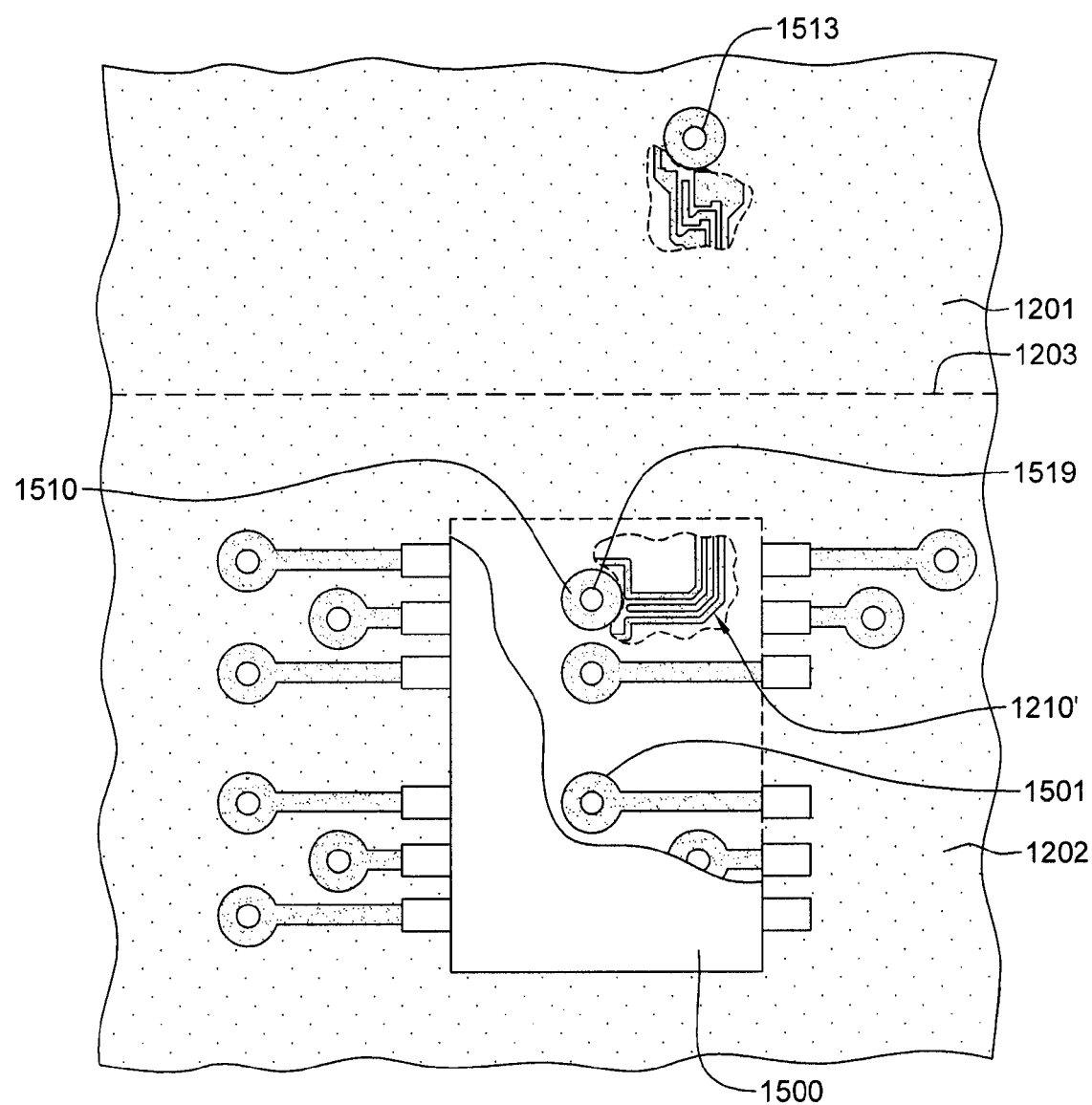
FIG. 15 is a partial cutaway plan view of a tamper-respondent assembly with a multilayer circuit board having an in situ vent structure with a vent opening in a secure volume of the tamper-respondent assembly, as well as a vent opening in an unsecure region of the tamper-respondent assembly below, for instance, an electronic component, in accordance with one or more aspects of the present invention.

By way of further example, FIG. 15 depicts a partial cutaway plan view of a tamper-respondent assembly with a multilayer circuit board having an in situ vent structure, such as in situ vent structure 1210' of FIG. 12B, described herein. In this implementation, a first vent opening 1513 is provided within the secure volume 1201 of the tamper-respondent assembly, and a second vent opening 1519 is provided within the unsecured region 1202 of the tamper-respondent assembly. As explained, the vent openings 1513, 1519 are in fluid communication with, for instance, respective embedded vent cavities of the in situ vent structure 1210', as well as the vent channels of the in situ vent structure 1210'. In this manner an air passage is established between the secure volume 1201 and the unsecured region 1202, across the secure boundary 1203 of the tamper-respondent assembly to allow for venting of the space within the secure volume 1201. In one or more implementations, the electric circuit layer containing the in situ vent structure 1210' may be disposed between a first tamper-detect network layer and a second tamper-detect network layer. To facilitate obscuring the presence of the in situ vent structure, vent opening 1519 may be positioned beneath a component 1500, such as an electronic component, in the unsecured region 1202 of the tamper-respondent assembly, and be aligned or positioned to mirror an electrical contact 1501 of electronic component 1500. Additionally, the vent openings may include round lands 1510, similar to round lands about a surface via 1501 of the tamper-respondent assembly, making detection of the in situ vent structure 1210', and in particular, the vent opening 1519, more difficult.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A tamper-respondent assembly comprising:
    a multilayer circuit board;
    a tamper-detection sensor embedded within the multilayer circuit board, the tamper-detection sensor defining, at least in part, a secure volume associated with the multilayer circuit board; and
    an in situ vent structure within the multilayer circuit board, the in situ vent structure comprising at least one vent channel, the at least one vent channel coupling in fluid communication a space within the secure volume and a space external to the secure volume to facilitate venting the space of the secure volume.

2. The tamper-respondent assembly of claim 1, wherein the in situ vent structure comprises, in part, multiple circuit line structures with a cover foil disposed over, at least in part, the multiple circuit line structures, the multiple circuit line structures being sized and configured to facilitate defining the in situ vent structure.

3. The tamper-respondent assembly of claim 2, wherein the at least one in situ vent structure resides within an electrical circuit layer of the multilayer circuit board.

4. The tamper-respondent assembly of claim 3, wherein the electrical circuit layer comprises a tamper-detect network layer of the embedded tamper-detection sensor within the multilayer circuit board.

5. The tamper-respondent assembly of claim 3, wherein circuit lines of the electrical circuit layer are formed of a conductive material and the multiple circuit line structures of the in situ vent structure are also formed of the conductive material.

6. The tamper-respondent assembly of claim 2, wherein at least one circuit line structure of two adjacent circuit line structures of the multiple circuit line structures of the in situ formed vent structure is configured to define at least one probing trap within the at least one vent channel of the in situ vent structure.

7. The tamper-respondent assembly of claim 2, further comprising:
    an enclosure coupled to the multilayer circuit board, the enclosure enclosing, at least in part, at least one electronic component to be protected; and
    a tamper-detection sensor over an inner surface of the enclosure, the tamper-detection sensor over the inner surface of the enclosure and the embedded tamper-detection sensor within the multilayer circuit board together facilitating defining the secure volume, wherein the at least one electronic component resides within the secure volume.

8. The tamper-respondent assembly of claim 7, wherein the multilayer circuit board includes at least one vent opening extending from a surface of the multilayer circuit board within the secure volume into the multilayer circuit board, the at least one vent opening in the multilayer circuit board being in fluid communication with the at least one vent channel of the in situ vent structure.

9. The tamper-respondent assembly of claim 8, wherein the in situ vent structure further comprises a vent cavity located within the secure volume, the vent cavity facilitating coupling in fluid communication the at least one vent opening extending into the multilayer circuit board and the at least one vent channel.

10. The tamper-respondent assembly of claim 9, wherein the vent cavity within the vent structure comprises a first vent cavity, and the at least one vent opening comprises at least one first vent opening, and wherein the in situ vent structure further includes a second vent cavity, the second vent cavity being located external to the secure volume, and the second vent cavity facilitating coupling in fluid communication at least one second vent opening extending, at least in part, into the multilayer circuit board and the at least one vent channel.

11. The tamper-respondent assembly of claim 10, wherein a second vent opening of the at least one second vent opening is hidden beneath a component in an unsecured region of the tamper-respondent assembly external to the secure volume.

12. The tamper-respondent assembly of claim 1, wherein the tamper-detection sensor embedded within the multilayer circuit board comprises multiple tamper-detect network layers, and wherein the in situ vent structure is located partially within the secure volume and is, at least in part, between a first tamper-detect network layer of the multiple tamper-detect network layers and a second tamper-detect network layer of the multiple tamper-detect network layers.

13. The tamper-respondent assembly of claim 12, wherein the in situ vent structure extends within the multilayer circuit board between the secure volume and an unsecure region of the multilayer circuit board external to the secure volume.

14. The tamper-respondent assembly of claim 1, further comprising multiple in situ vent structures within the multilayer circuit board, the in situ vent structure being one in situ vent structure of the multiple in situ vent structures, and wherein at least two in situ vent structures of the multiple in situ vent structures are located in different layers of the multilayer circuit board.

15. A tamper-respondent assembly comprising:
a multilayer circuit board;
a tamper-detection sensor embedded within the multilayer circuit board, the tamper-detection sensor defining, at least in part, a secure volume associated with the multilayer circuit board;
at least one electronic component disposed within a space within the secure volume; and
an in situ vent structure within the multilayer circuit board, the in situ vent structure comprising at least one vent channel, the at least one vent channel coupling in fluid communication the space within the secure volume and a space external to the secure volume to facilitate venting the space of the secure volume.

16. The tamper-respondent assembly of claim 15, wherein the in situ vent structure comprises, in part, multiple circuit line structures with a cover foil disposed over, at least in part, the multiple circuit line structures, the multiple circuit line structures being sized and configured to facilitate defining the in situ vent structure.

17. The tamper-respondent assembly of claim 16, wherein the in situ vent structure resides within an electrical circuit layer of the multilayer circuit board.

18. The tamper-respondent assembly of claim 15, further comprising:
an enclosure coupled to the multilayer circuit board, the enclosure enclosing, at least in part, at least one electronic component to be protected; and
a tamper-detection sensor over an inner surface of the enclosure, the tamper-detection sensor over the inner surface of the enclosure and the embedded tamper-detection sensor within the multilayer circuit board together facilitating defining the secure volume, wherein the at least one electronic component resides within the secure volume.

19. The tamper-respondent assembly of claim 18, wherein the multilayer circuit board includes at least one vent opening extending from a surface of the multilayer circuit board within the secure volume into the multilayer circuit board, the at least one vent opening in the multilayer circuit board being in fluid communication with the at least one vent channel of the in situ vent structure.

20. A fabrication method comprising:
fabricating a tamper-respondent assembly, the fabricating comprising:
providing a multilayer circuit board;
providing a tamper-detection sensor embedded within the multilayer circuit board, the tamper-detection sensor defining, at least in part, a secure volume associated with the multilayer circuit board; and
forming in place an in situ vent structure within the multilayer circuit board, the in situ vent structure including at least one vent channel, the at least one vent channel coupling in fluid communication a space within the secure volume and a space external to the secure volume to facilitate venting the space of the secure volume.

\* \* \* \* \*